(12) United States Patent
Kurihara et al.

(10) Patent No.: US 9,714,383 B2
(45) Date of Patent: Jul. 25, 2017

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Eriko Kurihara, Chiba (JP); Masayuki Saito, Chiba (JP); Yoshimasa Furusato, Chiba (JP); Kenji Hirata, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 10 days.

(21) Appl. No.: 14/903,056

(22) PCT Filed: Jun. 9, 2014

(86) PCT No.: PCT/JP2014/065241
§ 371 (c)(1),
(2) Date: Jan. 5, 2016

(87) PCT Pub. No.: WO2015/015904
PCT Pub. Date: Feb. 5, 2015

(65) Prior Publication Data
US 2016/0137922 A1    May 19, 2016

(30) Foreign Application Priority Data

Aug. 1, 2013  (JP) .................. 2013-160248

(51) Int. Cl.
| | | |
|---|---|---|
| G02F 1/1333 | (2006.01) |
| C09K 19/34 | (2006.01) |
| C07C 25/18 | (2006.01) |
| C09K 19/12 | (2006.01) |
| C09K 19/30 | (2006.01) |
| C07C 43/29 | (2006.01) |
| C07D 309/06 | (2006.01) |
| C07D 319/06 | (2006.01) |
| C09K 19/54 | (2006.01) |
| C07C 43/225 | (2006.01) |
| C09K 19/04 | (2006.01) |

(52) U.S. Cl.
CPC .......... *C09K 19/3402* (2013.01); *C07C 25/18* (2013.01); *C07C 43/225* (2013.01); *C07C 43/29* (2013.01); *C07D 309/06* (2013.01); *C07D 319/06* (2013.01); *C09K 19/12* (2013.01); *C09K 19/3003* (2013.01); *C09K 19/542* (2013.01); *C09K 2019/0466* (2013.01); *C09K 2019/124* (2013.01); *C09K 2019/3025* (2013.01); *C09K 2019/3422* (2013.01); *C09K 2019/548* (2013.01)

(58) Field of Classification Search
CPC   C09K 19/3402; C09K 19/12; C09K 19/3003; C09K 19/542; C09K 2019/0466; C09K 2019/124; C09K 2019/3025; C09K 2019/3422; C09K 2019/548; G02F 1/1333; C07C 25/18; C07C 43/29; C07C 43/225; C07D 309/06; C07D 319/06
USPC ............. 252/299.01, 299.6, 299.61; 428/1.1
See application file for complete search history.

(56) References Cited

U.S. PATENT DOCUMENTS

| | | | |
|---|---|---|---|
| 3,600,445 A | 8/1971 | Hermann et al. |
| 3,988,437 A | 10/1976 | Bradner |
| 5,126,214 A | 6/1992 | Tokailin et al. |
| 9,212,311 B2 * | 12/2015 | Lee ........................ C09K 19/12 |
| 2012/0119141 A1 | 5/2012 | Manabe et al. |
| 2012/0162595 A1 | 6/2012 | Lee et al. |

FOREIGN PATENT DOCUMENTS

| | | |
|---|---|---|
| DE | 3225741 | 2/1984 |
| DE | 102010025572 | 1/2012 |
| JP | 3-033183 | 2/1991 |
| JP | 3-162484 | 7/1991 |
| JP | 2012-533662 | 12/2012 |
| WO | 2011009524 | 1/2011 |
| WO | 2011029510 | 3/2011 |

OTHER PUBLICATIONS

"International Search Report (Form PCT/ISA/210)", mailed on Sep. 2, 2014, pp. 1-4.

* cited by examiner

*Primary Examiner* — Geraldina Visconti
(74) *Attorney, Agent, or Firm* — Jianq Chyun IP Office

(57) ABSTRACT

A liquid crystal composition having a suitable balance regarding at least one or two of characteristics such as a high maximum temperature of a nematic phase, a low minimum temperature of the nematic phase, small viscosity, suitable optical anisotropy, large positive dielectric anisotropy, large specific resistance, high stability to ultraviolet light and heat or a large elastic constant; and an AM device having a short response time, a large voltage holding ratio, a low threshold voltage, a large contrast ratio or a long service life. The composition has positive dielectric anisotropy and contains a specific compound having high stability to ultraviolet light as a first component, and a liquid crystal display device includes the composition.

20 Claims, No Drawings

LIQUID CRYSTAL COMPOSITION AND LIQUID CRYSTAL DISPLAY DEVICE

TECHNICAL FIELD

The invention relates to a liquid crystal composition, a liquid crystal display device including the composition, and so forth. In particular, the invention relates to a liquid crystal composition having a positive dielectric anisotropy, and an active matrix (AM) device that includes the liquid crystal composition and has a mode such as a TN mode, an OCB mode, an IPS mode, an FFS mode or an FPA mode. The invention also relates to a liquid crystal display device having a polymer sustained alignment mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) or a field induced photo-reactive alignment (FPA) mode. A classification based on a driving mode in the device includes a passive matrix (PM) and an active matrix (AM). The PM is classified into static and multiplex and so forth. The AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the liquid crystal composition relates to a response time of the device. A short response time is preferred for displaying moving images on the device. A shorter response time even by one millisecond is desirable. Accordingly, a small viscosity of the composition is preferred. A small viscosity at a low temperature is further preferred. An elastic constant of the composition relates to a contrast of the device. In order to increase the contrast of the device, a large elastic constant in the composition is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A liquid crystal composition can be injected into a liquid crystal display device in a short time.

An optical anisotropy of the composition relates to a contrast ratio in the device. According to a mode of the device, a large optical anisotropy or a small optical anisotropy, more specifically, a suitable optical anisotropy is required. A product (Δn×d) of the optical anisotropy (Δn) of the composition and a cell gap (d) in the device is designed so as to maximize the contrast ratio. A suitable value of the product depends on a type of the operating mode. In a device having a mode such as TN, a suitable value is about 0.45 micrometer. In the above case, a composition having the large optical anisotropy is preferred for a device having a small cell gap. A large dielectric anisotropy in the composition contributes to a low threshold voltage, a small electric power consumption and a large contrast ratio in the device. Accordingly, the large dielectric anisotropy is preferred. A large specific resistance in the composition contributes to a large voltage holding ratio and the large contrast ratio in the device. Accordingly, a composition having the large specific resistance at room temperature and also at a temperature close to the maximum temperature of the nematic phase in an initial stage is preferred. The composition having the large specific resistance at room temperature and also at a temperature close to the maximum temperature of the nematic phase after the device has been used for a long period of time is preferred. Stability of the composition to ultraviolet light and heat relates to a service life of the liquid crystal display device. In the cases where the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of the polymerizable compound is added is injected into the device. Then, the composition is irradiated with ultraviolet light while voltage is applied between substrates of the device. The polymerizable compound is polymerized to form a network structure of the polymer in the liquid crystal composition. In the composition, alignment of liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

A composition having a positive dielectric anisotropy is used in an AM device having the TN mode. In an AM device having the VA mode, a composition having a negative dielectric anisotropy is used. A composition having the positive or negative dielectric anisotropy is used in an AM device having the IPS mode or the FFS mode. In an AM device of the polymer sustained alignment mode, a composition having the positive or negative dielectric anisotropy is used. An example of a liquid crystal composition relates to the invention is disclosed in Patent literature Nos. 1 and 2. An example of a composition for a device having the polymer sustained alignment (PSA) mode is disclosed in patent literature No. 3.

CITATION LIST

Patent Literature

Patent literature No. 1: DE 102010025572 A1.
Patent literature No. 2: WO 2011-009524 A.
Patent literature No. 3: WO 2011-029510 A.

SUMMARY OF THE INVENTION

Technical Problem

One of aims of the invention is to provide a liquid crystal composition satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. Another aim is to provide a liquid crystal composition having a suitable balance regarding at least two of the characteristics. Another aim is to provide a liquid crystal display device including such a composition. Another aim is to provide an AM device having characteristics such as a short response time, a large voltage holding ratio, a low threshold voltage, a large contrast ratio and a long service life.

Solution to Problem

The invention concerns a liquid crystal composition that has a positive dielectric anisotropy and contains at least one compound selected from the group of compounds represented by formula (1) as a first component, and concerns a liquid crystal display device including the composition:

dently fluorine, chlorine, or alkyl having 1 to 12 carbons in which at least one of hydrogen may be replaced by fluorine; $Z^1$, $Z^2$, $Z^3$ and $Z^4$ are independently a single bond, —$CH_2CH_2$—, —$CH_2O$—, —$OCH_2$—, —COO— or —OCO—; a, b and c are independently 0, 1, 2, 3 or 4; and d is 0, 1 or 2.

Advantageous Effects of Invention

An advantage of the invention is a liquid crystal composition satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. Another advantage is a liquid crystal composition having a suitable balance regarding at least two of the characteristics. Another advantage is a liquid crystal display device including such a composition. Another advantage is an AM device having characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and dielectric anisotropy. The compound has a six-membered ring such as 1,4-cyclohexylene and 1,4-phenylene, and rod like molecular structure.

"Polymerizable compound" is added for the purpose of forming a polymer in the composition. At least one compound selected from the group of compounds represented by

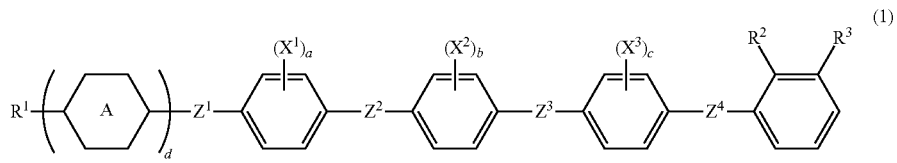

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, and one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are indepenformula (1) may be occasionally abbreviated as "compound (1)." "Compound (1)" means one compound represented by formula (1), a mixture of two compounds, or a mixture of three or more compounds. A same rule applies also to any other compound represented by any other formula.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator and a polymerization inhibitor is added to the composition when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A ratio of the polymerization initiator and the polymerization inhibitor is exceptionally expressed based on the weight of the polymerizable compound.

"Maximum temperature of the nematic phase" may be occasionally abbreviated as "maximum temperature." "Minimum temperature of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and the composition has the large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in the initial stage, and the device has the large voltage holding ratio at room temperature and also at a temperature close to the maximum temperature of the nematic phase even after the device has been used for the long period of time.

An expression "at least one of 'A' may be replaced by 'B'" means that the number of 'A' is arbitrary. When the number of 'A' is 1, a position of 'A' is arbitrary, and also when the number of 'A' is 2 or more, positions thereof can be selected without restriction. A same rule applies also to an expression "at least one of 'A' is replaced by 'B'."

A symbol of terminal group $R^1$ is used for a plurality of compounds in chemical formulas of component compounds. In the compounds, two groups represented by two of arbitrary $R^1$ may be identical or different. In one case, for example, $R^1$ of compound (1) is ethyl and $R^1$ of compound (1-1) is ethyl. In another case, for example, $R^1$ of compound (1) is ethyl and $R^1$ of compound (1-1) is propyl. A same rule applies also to a symbol of $R^3$, $X^1$ or the like. In formula (1), when d is 2, two of ring A exists. In the compound, two rings represented by two of ring A may be identical or different. A same rule applies also to two of arbitrary ring A when d is larger than 2. A same rule applies also to a symbol of $Z^5$ and a ring C or the like.

Then, 2-fluoro-1,4-phenylene means two divalent groups described below. In a chemical formula, fluorine may be leftward (L) or rightward (R). A same rule applies also to a divalent group of asymmetrical ring such as tetrahydropyran-2,5-diyl.

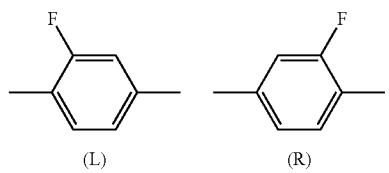

(L)  (R)

In compound (1), a perpendicular line crossing a benzene ring means that arbitrary hydrogen on the benzene ring may be replaced by $X^1$ or the like. A subscript such as a represents the number of $X^1$ subjected to replacement. A same rule applies also to compound (1-1) or the like. In compound (4), a perpendicular line crossing a hexagonal shape means that arbitrary hydrogen on a six-membered ring may be replaced by $P^1$-$Sp^1$ or the like. A subscript such as h represents the number of $P^1$-$Sp^1$ subjected to replacement. In a group such as group (P-1) or the like, a wavy line represents a site to form a bonding.

The invention includes the items described below.

Item 1. A liquid crystal composition that has a positive dielectric anisotropy, and contains at least one compound selected from the group of compounds represented by formula (1) as a first component:

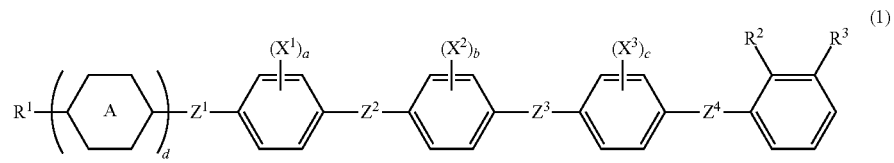

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, and one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; $Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

Item 2. The liquid crystal composition according to item 1, containing at least one compound selected from the group of compounds represented by formulas (1-1) to (1-3) as the first component:

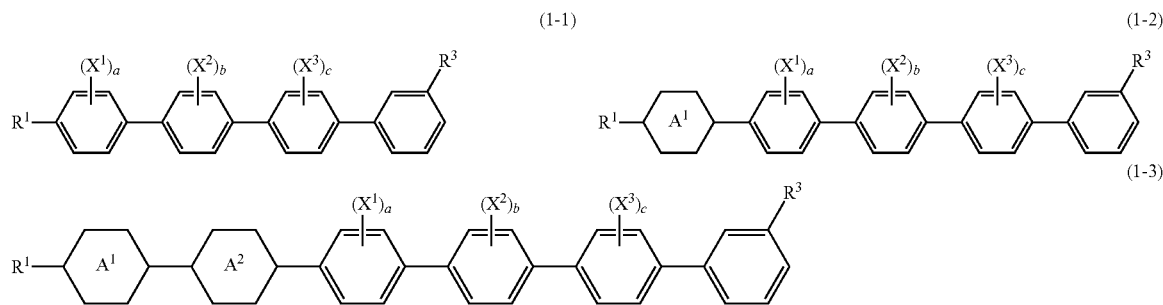

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; and a, b and c are independently 0, 1, 2, 3 or 4.

Item 3. The liquid crystal composition according to item 1 or 2, containing at least one compound selected from the group of compounds represented by formulas (1-1-1) to (1-1-9), formula (1-2-1) and formula (1-2-2) as the first component:

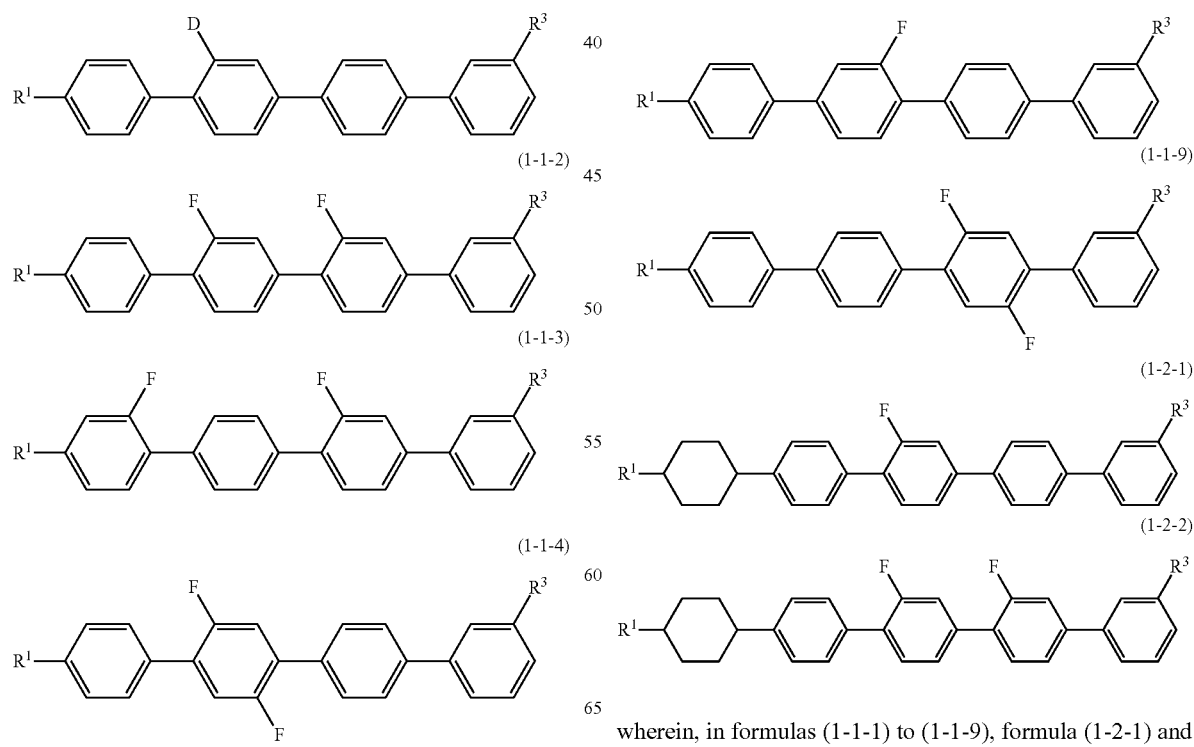

wherein, in formulas (1-1-1) to (1-1-9), formula (1-2-1) and formula (1-2-2), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 4. The liquid crystal composition according to any one of claims 1 to 3, wherein a ratio of the first component is in the range of 0.03% by weight to 10% by weight based on the weight of the liquid crystal composition.

Item 5. The liquid crystal composition according to any one of items 1 to 4, containing at least one compound selected from the group of compounds represented by formula (2) as a second component:

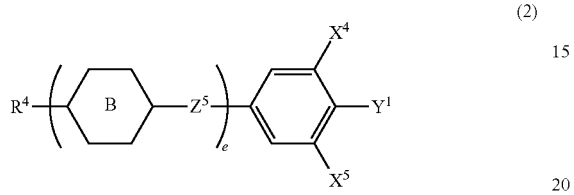

(2)

wherein, in formula (2), $R^4$ is alkyl having 1 to 12 carbons, alkoxy having 1 to 12 carbons or alkenyl having 2 to 12 carbons; ring B is 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl or tetrahydropyran-2,5-diyl; $Z^5$ is a single bond, —$CH_2CH_2$—, —COO— or —$CF_2O$—; $X^4$ and $X^5$ are independently hydrogen or fluorine; $Y^1$ is fluorine, chlorine, alkyl having 1 to 12 carbons in which at least one of hydrogen is replaced by halogen, alkoxy having 1 to 12 carbons in which at least one of hydrogen is replaced by halogen, or alkenyloxy having 2 to 12 carbons in which at least one of hydrogen is replaced by halogen; and e is 1, 2, 3 or 4.

Item 6. The liquid crystal composition according to any one of items 1 to 5, containing at least one compound selected from the group of compounds represented by formulas (2-1) to (2-27) as the second component:

(2-1)

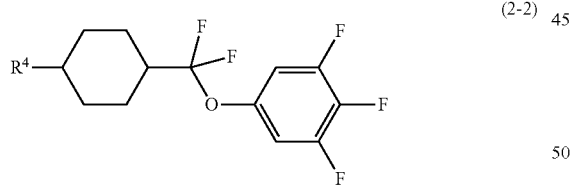

(2-2)

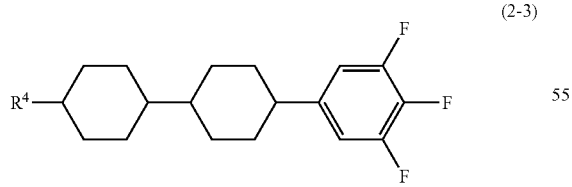

(2-3)

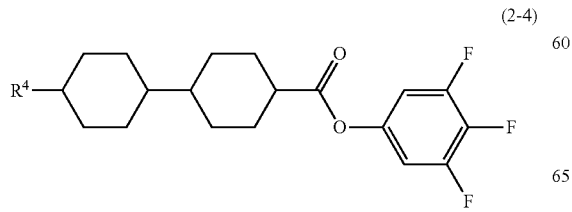

(2-4)

-continued

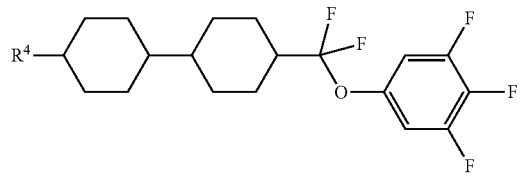

(2-5)

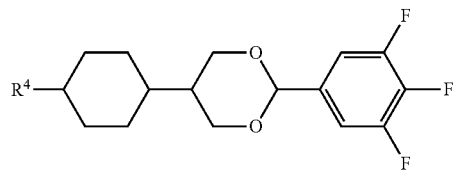

(2-6)

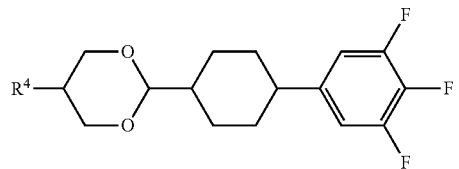

(2-7)

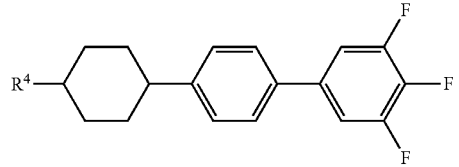

(2-8)

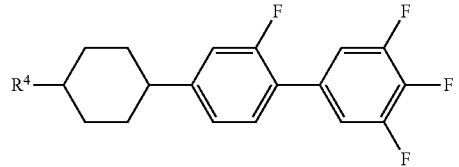

(2-9)

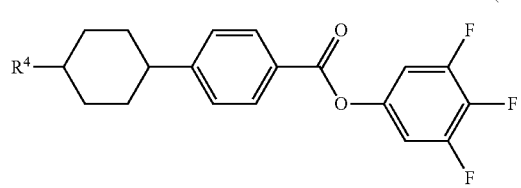

(2-10)

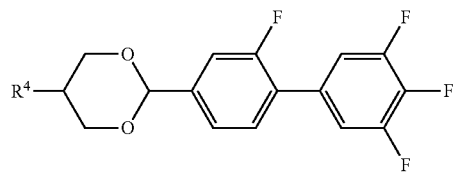

(2-11)

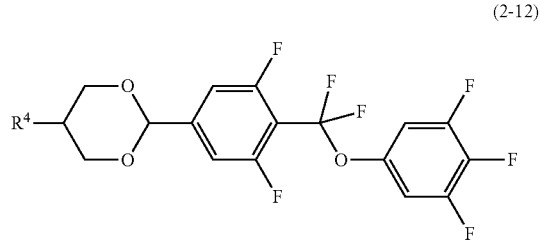

(2-12)

-continued
(2-13)
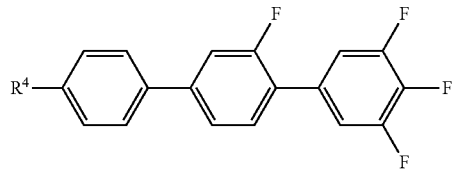
(2-14)
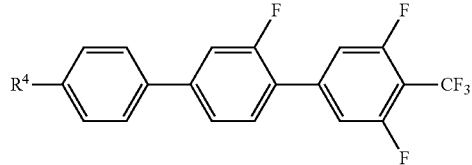
(2-15)
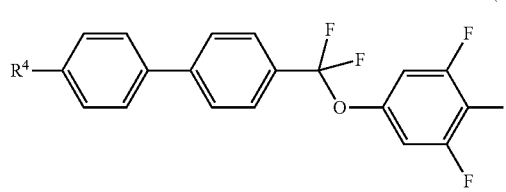
(2-16)
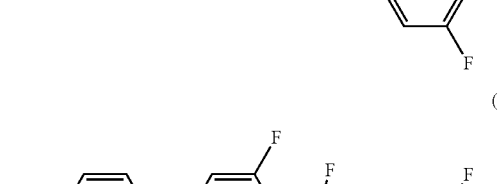
(2-17)
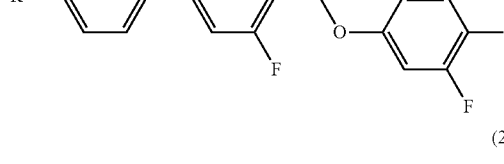
(2-18)
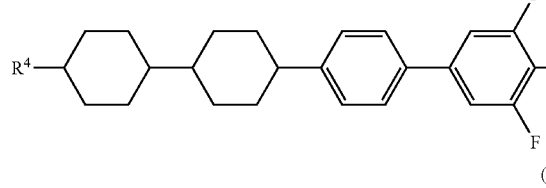
(2-19)
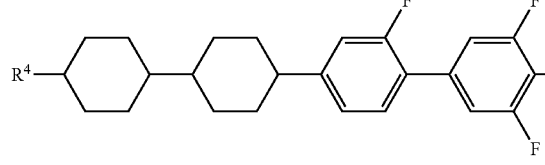
(2-20)
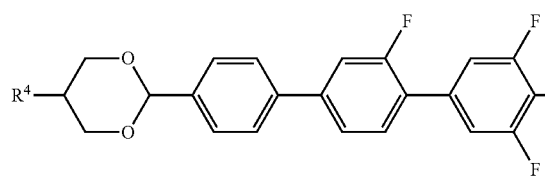
-continued
(2-21)
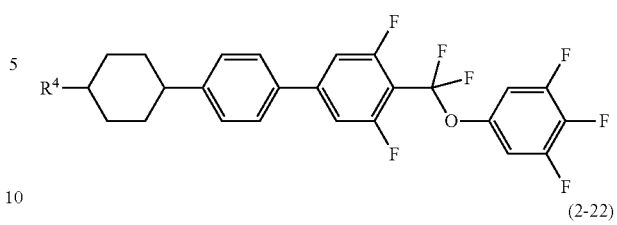
(2-22)
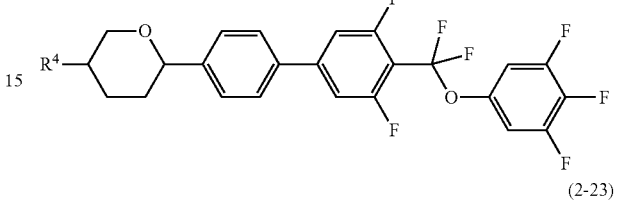
(2-23)
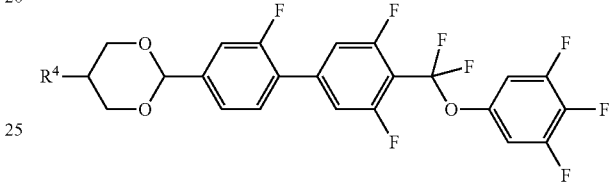
(2-24)
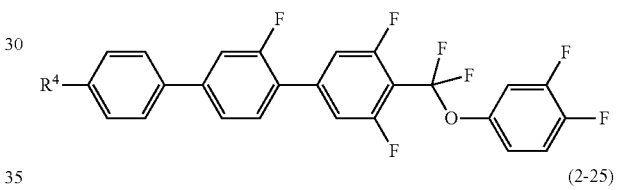
(2-25)
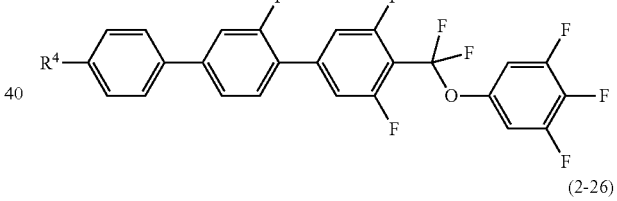
(2-26)
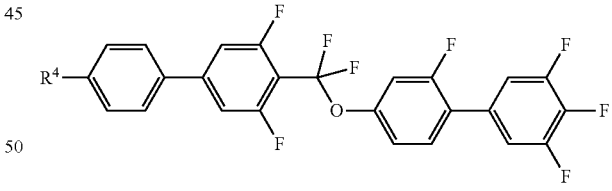
(2-27)
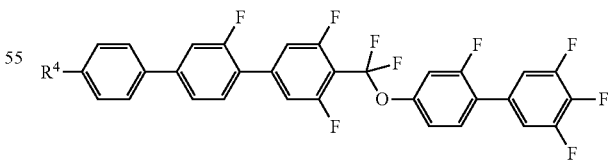
wherein, in formula (2-1) to formula (2-27), $R^4$ is alkyl having 1 to 12 carbons, alkoxy having 1 to 12 carbons or alkenyl having 2 to 12 carbons.
Item 7. The liquid crystal composition according to item 5 or 6, wherein a ratio of the second component is in the range of 10% by weight to 85% by weight based on the weight of the liquid crystal composition.

Item 8. The liquid crystal composition according to any one of items 1 to 7, further containing at least one compound selected from the group of compounds represented by formula (3) as a third component:

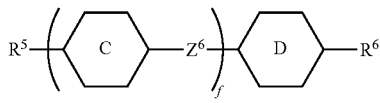
(3)

wherein, in formula (3), $R^5$ and $R^6$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring C and ring D are independently 1,4-cyclohexylene, 1,4-phenylene, 2-fluoro-1,4-phenylene or 2,5-difluoro-1,4-phenylene; $Z^6$ is a single bond, —CH$_2$CH$_2$—, —CH$_2$O—, —OCH$_2$—, —COO— or —OCO—; and f is 1, 2 or 3.

Item 9. The liquid crystal composition according to any one of items 1 to 8, containing at least one compound selected from the group of compounds represented by formulas (3-1) to (3-13) as the third component:

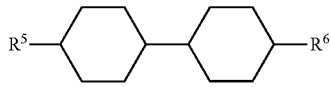
(3-1)

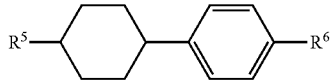
(3-2)

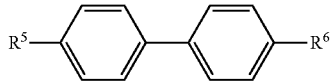
(3-3)

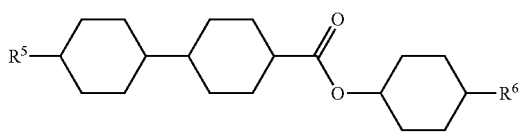
(3-4)

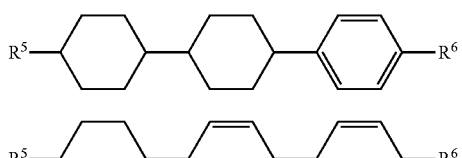
(3-5)

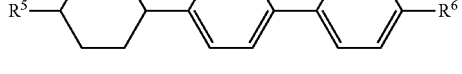
(3-6)

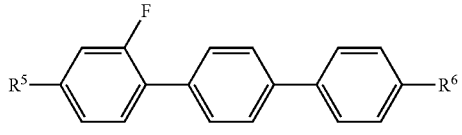
(3-7)

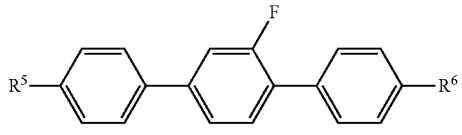
(3-8)

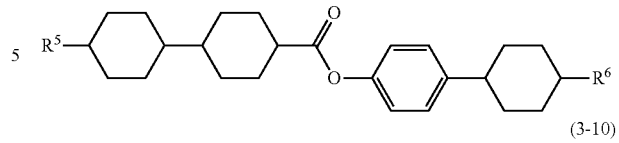
(3-9)

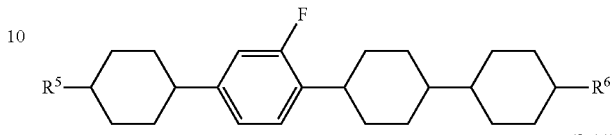
(3-10)

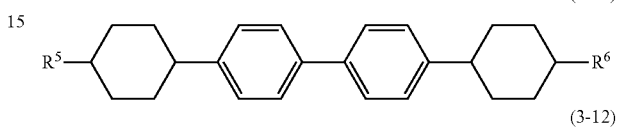
(3-11)

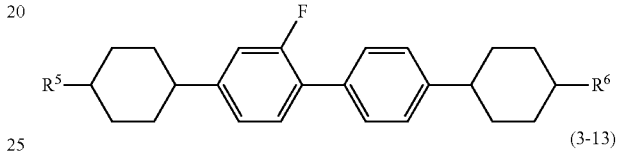
(3-12)

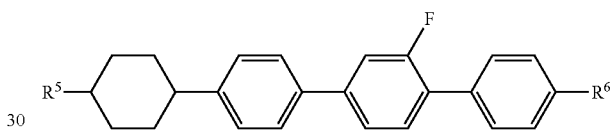
(3-13)

wherein, in formula (3-1) to formula (3-13), $R^5$ and $R^6$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 10. The liquid crystal composition according to item 8 or 9, wherein a ratio of the third component is in the range of 5% by weight to 70% by weight based on the weight of the liquid crystal composition.

Item 11. The liquid crystal composition according to any one of items 1 to 10, containing at least one polymerizable compound selected from the group of compounds represented by formula (4) as an additive component:

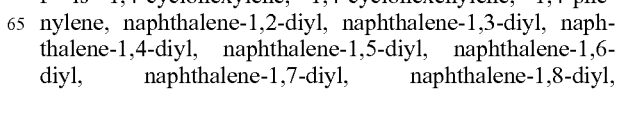
(4)

wherein, in formula (4), ring E and ring G are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; ring F is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; $Z^7$ and $Z^8$ are independently a single bond or alkylene having 1 to 10 carbons, and in the alkylene, at least one of —$CH_2$— may be replaced by —O—, —CO—, —COO— or —COO—, and at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine; $P^1$, $P^2$ and $P^3$ are a polymerizable group; $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine; g is 0, 1 or 2; and h, j and k are independently 0, 1, 2, 3 or 4, and a sum of h, j and k is 1 or more.

Item 12. The liquid crystal composition according to item 11, wherein, in formula (4) described in item 11, $P^1$, $P^2$ and $P^3$ are independently a polymerizable group selected from the group of groups represented by formulas (P-1) to (P-5):

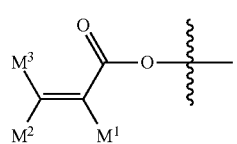

(P-1)

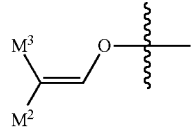

(P-2)

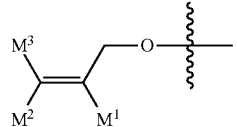

(P-3)

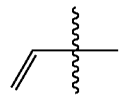

(P-4)

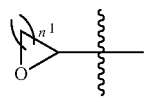

(P-5)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (P-5), $n^1$ is 1, 2, 3 or 4; when both $P^1$ and $P^3$ are a group represented by formula (P-4), at least one of $Sp^1$ and $Sp^3$ is alkylene in which at least one of —$CH_2$— is replaced by —O—, —COO—, —OCO— or —OCOO—.

Item 13. The liquid crystal composition according to any one of items 1 to 12, containing at least one polymerizable compound selected from the group of compounds represented by formulas (4-1) to (4-27) as the additive component:

(4-1)

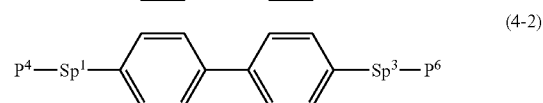

(4-2)

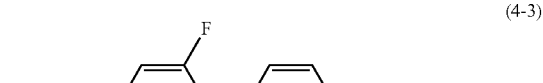

(4-3)

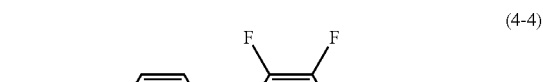

(4-4)

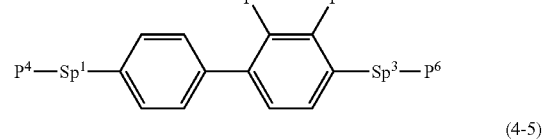

(4-5)

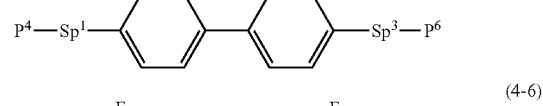

(4-6)

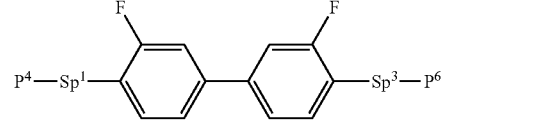

(4-7)

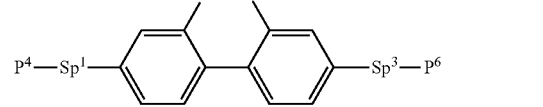

(4-8)

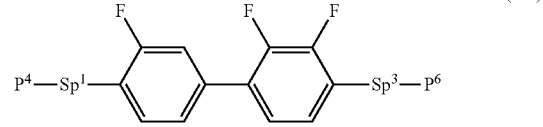

(4-9)

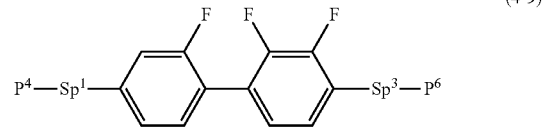

(4-10)

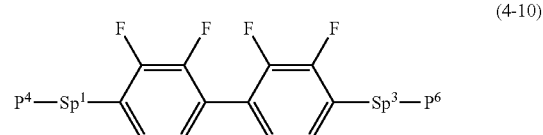

(4-11)

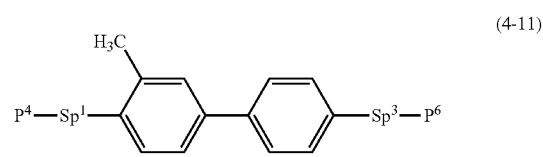

(4-12)
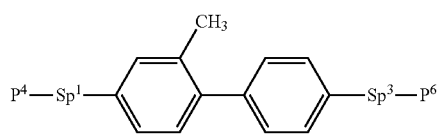
(4-13)
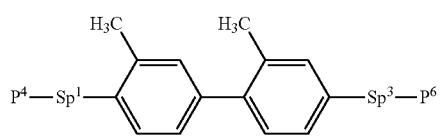
(4-14)
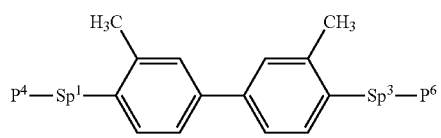
(4-15)
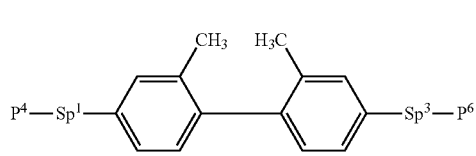
(4-16)
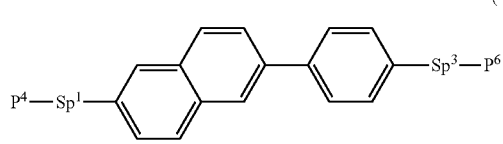
(4-17)
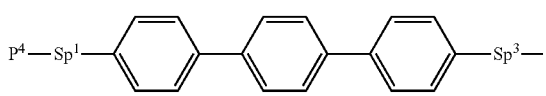
(4-18)
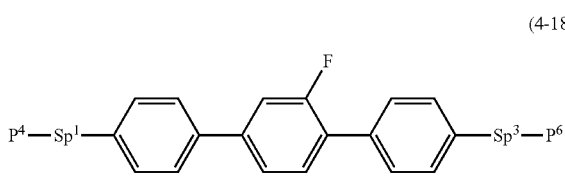
(4-19)
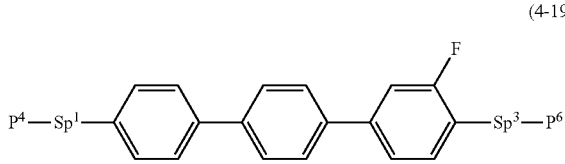
(4-20)
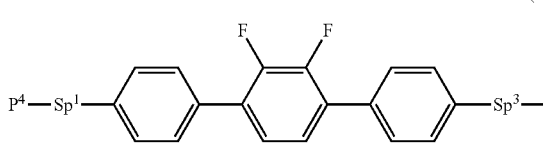
(4-21)
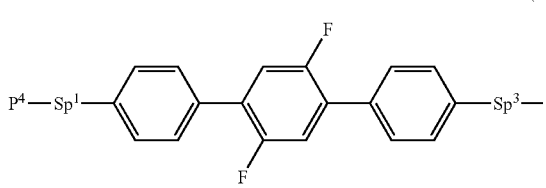
(4-22)
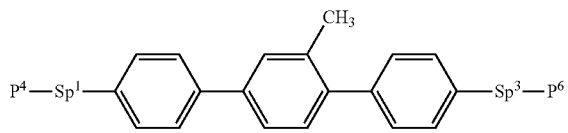
(4-23)
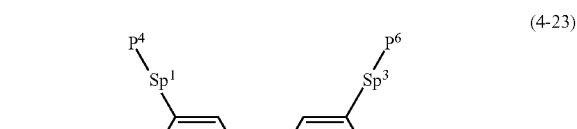
(4-24)
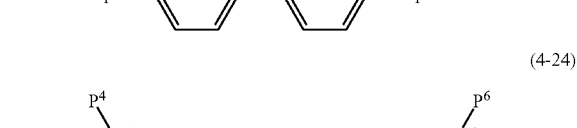
(4-25)
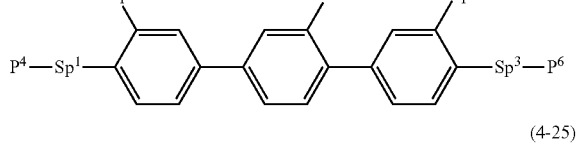
(4-26)
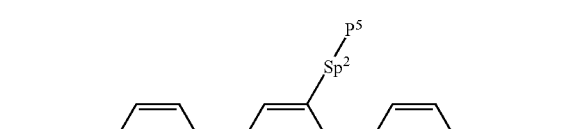
(4-27)
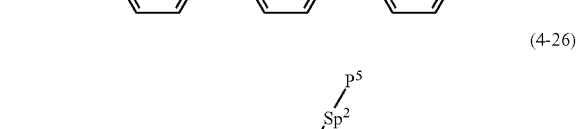
wherein, in formula (4-1) to formula (4-27), $P^4$, $P^5$ and $P^6$ are independently a group represented by formulas (P-1) to (P-3);
(P-1)
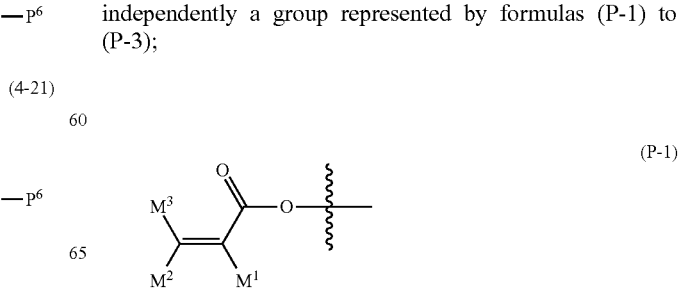

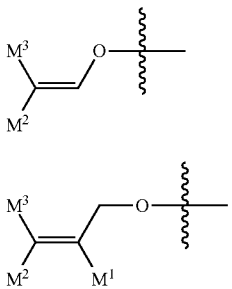

(P-2)

(P-3)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (4-1) to formula (4-27), $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$—CH$_2$— may be replaced by —CH=CH— or —C≡C—, and in the groups, at least one of hydrogen may be replaced by fluorine or chlorine.

Item 14. The liquid crystal composition according to any one of items 11 to 13, wherein a ratio of addition of the additive component is in the range of 0.03% by weight to 10% by weight, based on the weight of the liquid crystal composition before adding an additive thereto.

Item 15. A compound represented by formula (1):

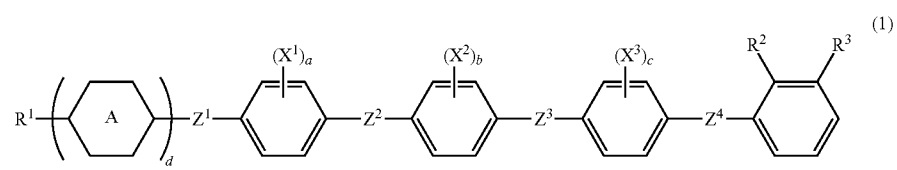

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, and one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; $Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

Item 16. The compound according to item 15, represented by any one of formulas (1-1) to (1-3):

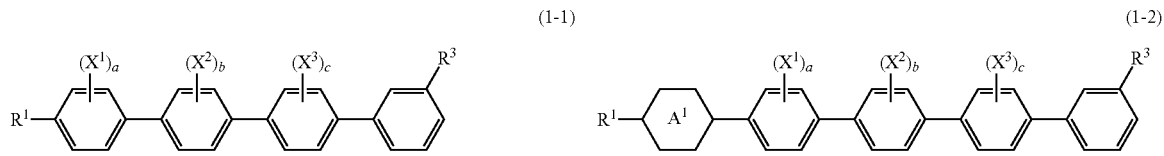

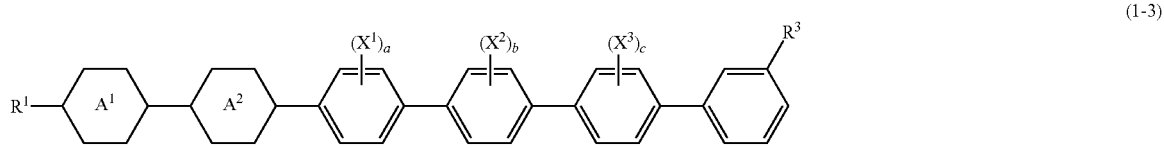

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine or methyl; and a, b, and c are independently 0, 1, 2, 3 or 4.

Item 17. The compound according to item 15 or 16, represented by any one of formulas (1-1-1) to (1-1-9), formula (1-2-1) and formula (1-2-2):

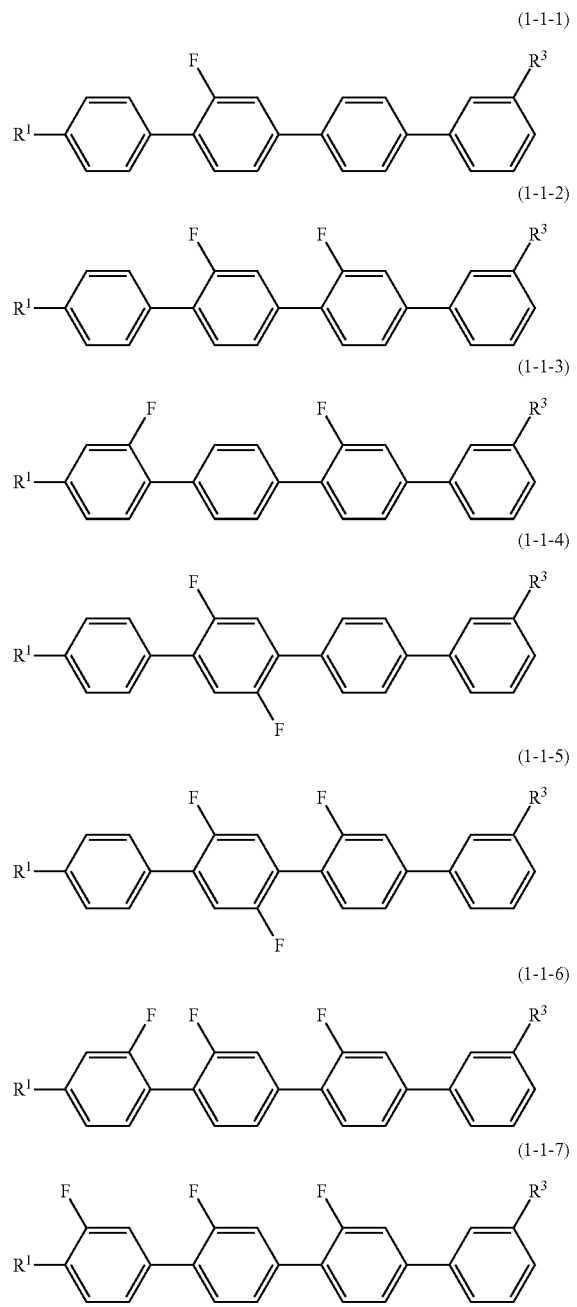

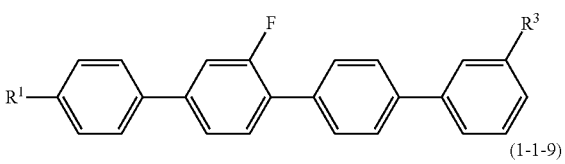

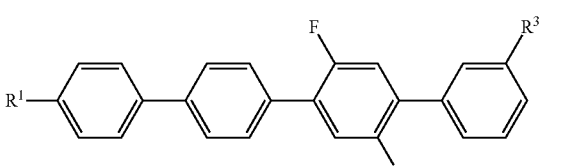

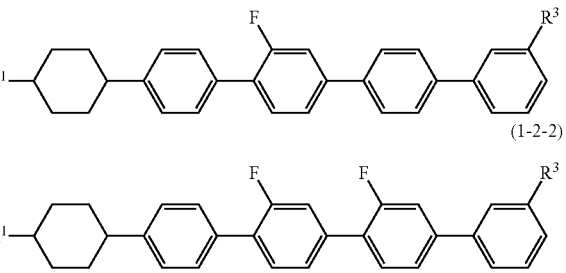

wherein, in formulas (1-1-1) to (1-1-9), formula (1-2-1) and formula (1-2-2), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 18. A liquid crystal display device, including the liquid crystal composition according to any one of items 1 to 14.

Item 19. The liquid crystal display device according to item 18, wherein an operating mode in the liquid crystal display device is an IPS mode, a VA mode, an FFS mode or an FPA mode, and a driving mode in the liquid crystal display device is an active matrix mode.

Item 20. A polymer sustained alignment mode liquid crystal display device, wherein the liquid crystal display device includes the liquid crystal composition according to any one of items 11 to 14, and a polymerizable compound in the composition is polymerized.

Item 21. Use of the liquid crystal composition according to any one of items 1 to 14 in a liquid crystal display device.

Item 22. Use of the liquid crystal composition according to any one of items 11 to 14 in a polymer sustained alignment mode liquid crystal display device.

The invention further includes the following items: (a) the composition, further containing at least one of additives such as an optically active compound, an antioxidant, an ultraviolet light absorber, a dye, an antifoaming agent, a polymerizable compound, a polymerization initiator or a polymerization inhibitor; (b) an AM device including the composition; (c) the composition further containing a polymerizable compound, and a polymer sustained alignment (PSA) mode AM device including the composition; (d) a polymer sustained alignment (PSA) mode AM device, wherein the device includes the composition, and a polymerizable compound in the composition is polymerized; (e) a device including the composition and having the PC mode, the TN mode, the STN mode, the ECB mode, the OCB mode, the IPS mode, the VA mode, the FFS mode or the FPA mode; (f) a transmissive device including the composition; (g) use of the composition as the composition having the nematic phase; and (h) use as an optically active composition by adding the optically active compound to the composition.

The composition of the invention will be described in the following order. First, a constitution of the component compounds in the composition will be described. Second, main characteristics of the component compounds and main effects of the compounds on the composition will be described. Third, a combination of components in the composition, a preferred ratio of the components and the basis thereof will be described. Fourth, a preferred embodiment of the component compounds will be described. Fifth, a preferred component compounds will be shown. Sixth, an additive that may be added to the composition will be described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, an additive or the like in addition to the compound selected from compound (1), compound (2), compound (3) and compound (4). An expression "any other liquid crystal compound" means a liquid crystal compound different from compound (1), compound (2) and compound (3). Such a compound is mixed with the composition for the purpose of further adjusting the characteristics. The additive is the optically active compound, the antioxidant, the ultraviolet light absorber, the dye, the antifoaming agent, the polymerizable compound, the polymerization initiator, the polymerization inhibitor or the like.

Composition B consists essentially of liquid crystal compounds selected from compound (1), compound (2), compound (3) and compound (4). A term "essentially" means that the composition may contain the additive, but contains no any other liquid crystal compound. Composition B has a smaller number of components than composition A has. Composition B is preferred to composition A in view of cost reduction. Composition A is preferred to composition B in view of possibility of further adjusting the characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium" and a symbol S stands for "small" or "low." The symbols L, M and S represent a classification based on a qualitative comparison among the component compounds, and 0(zero) means "a value is nearly zero."

TABLE 2

Characteristics of Compounds

| Compounds | Compound (1) | Compound (2) | Compound (3) |
|---|---|---|---|
| Maximum temperature | L | S to L | S to L |
| Viscosity | M to L | M to L | S to M |
| Optical anisotropy | L | M to L | S to L |
| Dielectric anisotropy | 0 | S to L | 0 |
| Specific resistance | L | L | L |

Upon mixing the component compounds with the composition, the main effects of the component compounds on the characteristics of the composition are as described below. Compound (1) maintains a high stability to ultraviolet light. Compound (2) increases the dielectric anisotropy. Compound (3) increases the maximum temperature or decreases the viscosity.

Third, the combination of components in the composition, the preferred ratio of the component compounds and the basis thereof will be described. A preferred combination of components in the composition includes a combination of the first component and the second component, a combination of the first component and the second component and the third component, a combination of the first component and the second component and the additive component and a combination of the first component and the second component and the third component and the additive component. The combination of components in a preferred composition includes a combination of the first component and the second component and the third component.

A preferred ratio of the first component is about 0.03% by weight or more for maintaining the high stability to ultraviolet light, and about 10% by weight or less for decreasing the minimum temperature, based on the weight of the liquid crystal composition. A further preferred ratio is in the range of about 0.1% by weight to about 2% by weight. A particularly preferred ratio is in the range of about 0.3% by weight to about 1.5% by weight.

A preferred ratio of the second component is about 10% by weight or more for increasing the dielectric anisotropy, and about 85% by weight or less for decreasing the minimum temperature. A further preferred ratio is in the range of about 20% by weight to about 80% by weight. A particularly preferred ratio is in the range of about 40% by weight to about 75% by weight.

A preferred ratio of the third component is about 5% by weight or more for increasing the maximum temperature or decreasing the viscosity, and about 70% by weight or less for increasing the dielectric anisotropy. A further preferred ratio is in the range of about 15% by weight to about 60% by weight. A particularly preferred ratio is in the range of about 25% by weight to about 55% by weight.

Compound (4) is added to the composition for the purpose of adapting the composition for the polymer sustained alignment mode device. A preferred ratio of the additive is about 0.03% by weight or more for aligning the liquid crystal molecules, and about 10% by weight or less for preventing poor display in the device, based on the weight of the liquid crystal composition before adding an additive thereto. A further preferred ratio is in the range of about 0.1% by weight to about 2% by weight. A particularly preferred ratio is in the range of about 0.2% by weight to about 1% by weight.

Fourth, the preferred embodiment of the component compounds will be described. In compound (1) to compound (3), $R^1$, $R^2$, $R^3$, $R^5$ and $R^6$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, in which one of $R^2$ and $R^3$ may be hydrogen; When one of $R^2$ and $R^3$ is hydrogen, $R^2$ preferably includes hydrogen. A preferred $R^1$, $R^2$ or $R^3$ is alkyl having 1 to 12 carbons for increasing the stability, and alkenyl having 2 to 12 carbons for decreasing the minimum temperature. Preferred $R^5$ or $R^6$ is alkyl having 1 to 12 carbons for increasing the stability to ultraviolet light or heat or the like, and alkenyl having 2 to 12 carbons for decreasing the minimum temperature or decreasing the viscosity. R⁴ is alkyl having 1 to 12 carbons, alkoxy having 1 to 12 carbons or alkenyl having 2 to 12 carbons. Preferred $R^4$ is alkyl having 1 to 12 carbons for increasing the stability to ultraviolet light or heat.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH=CH— in the alkenyl depends on a position of a double bond. Trans is preferred in alkenyl such as 1-propenyl, 1-butenyl, 1-pentenyl, 1-hexenyl, 3-pentenyl and 3-hexenyl for decreasing the viscosity, for instance. Cis is preferred in alkenyl such as 2-butenyl, 2-pentenyl and 2-hexenyl. In the alkenyl, straight-chain alkenyl is preferred to branched-chain alkenyl.

Preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Alkyl is straight-chain alkyl or branched-chain alkyl, but includes no cyclic alkyl. Straight-chain alkyl is preferred to branched-chain alkyl. A same rule applies also to alkoxy, alkenyl or alkenyl in which at least one of hydrogen is replaced by fluorine. With regard to a configuration of 1,4-cyclohexylene, trans is preferred to cis for increasing the maximum temperature.

Ring A, ring $A^1$ and ring $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl. Preferred ring A, ring $A^1$ or ring $A^2$ is 1,4-cyclohexylene for decreasing the minimum temperature.

Ring B is 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl, or tetrahydropyran-2,5-diyl. Preferred ring B is 1,4-phenylene or 2-fluoro-1,4-phenylene for increasing the optical anisotropy. With regard to the configuration of 1,4-cyclohexylene, trans is preferred to cis for increasing the maximum temperature. Tetrahydropyran-2,5-diyl includes:

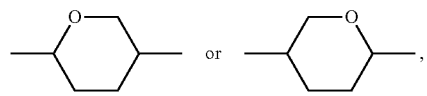

preferably

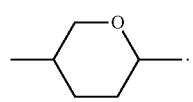

Ring C and ring D are independently 1,4-cyclohexylene, 1,4-phenylene, 2-fluoro-1,4-phenylene or 2,5-difluoro-1,4-phenylene; $Z^6$ is a single bond, —CH₂CH₂—, —CH₂O—, —OCH₂—, —COO— or —OCO—. Preferred ring C or ring D is 1,4-cyclohexylene for decreasing the viscosity, or 1,4-phenylene for increasing the optical anisotropy.

$X^1$, $X^2$ and $X^3$ are independently fluorine, chlorine, or alkyl having 1 to 12 carbons in which at least one of hydrogen may be replaced by fluorine. Preferred $X^1$, $X^2$ or $X^3$ is fluorine for decreasing the minimum temperature.

$X^4$ and $X^5$ are independently hydrogen or fluorine. Preferred $X^4$ or $X^5$ is fluorine for increasing the dielectric anisotropy.

$Y^1$ is fluorine, chlorine, alkyl having 1 to 12 carbons in which at least one of hydrogen is replaced by halogen, or alkoxy having 1 to 12 carbons in which at least one of hydrogen is replaced by halogen. Preferred halogen is fluorine or chlorine. Further preferred halogen is fluorine. Preferred $Y^1$ is fluorine for decreasing the minimum temperature.

$Z^1$, $Z^2$, $Z^3$, $Z^4$ and $Z^6$ are independently a single bond, —CH₂CH₂—, —CH₂O—, —OCH₂—, —COO— or —OCO—. Preferred $Z^1$, $Z^2$, $Z^3$ or $Z^4$ is a single bond for increasing the stability. Preferred $Z^6$ is a single bond for decreasing the viscosity.

$Z^5$ is a single bond, —CH₂CH₂—, —COO— or —CF₂O—. Preferred $Z^5$ is —CF₂O— for increasing the dielectric anisotropy.

Then, a, b and c are independently 0, 1, 2, 3 or 4. Preferred a, b or c is 1 or 2 for decreasing the minimum temperature, and 0 for increasing the maximum temperature. Then, d is 0, 1 or 2. Preferred d is 0 for decreasing the minimum temperature. Then, e is 1, 2, 3 or 4. Preferred e is 2 for decreasing the minimum temperature. Then, f is 1, 2 or 3. Preferred f is 2 for increasing the maximum temperature.

In compound (4), $P^1$, $P^2$ and $P^3$ are independently a polymerizable group. Preferred $P^1$, $P^2$ or $P^3$ is a polymerizable group selected from the group of groups represented by formula (P-1) to formula (P-5). Preferred $P^1$, $P^2$ or $P^3$ is group (P-1) and group (P-2). Further preferred group (P-1) is —OCO—CH=CH₂ and —OCO—C(CH₃)=CH₂. A wavy line from group (P-1) to group (P-5) represents a site to form a bonding.

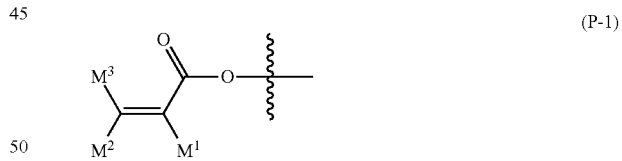

(P-1)

(P-2)

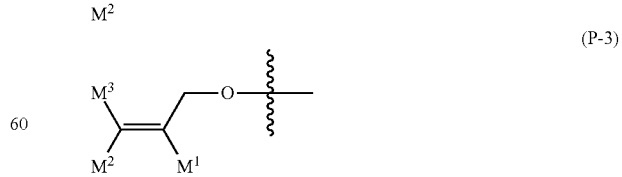

(P-3)

(P-4)

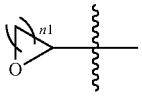 (P-5)

When all of $P^1$, $P^2$ and $P^3$ are group (P-1), $M^1$ (or $M^2$, or $M^3$) of $P^1$, $M^1$ of $P^2$ or $M^1$ of $P^3$ may be identical or different. In group (P-1), $M^1$, $M^2$ and $M^3$ are independently hydrogen, fluorine, alkyl having 1 to 5 carbons, or alkyl having 1 to 5 carbons in which at least one of hydrogen is replaced by halogen. Preferred $M^1$, $M^2$ or $M^3$ is hydrogen or methyl for increasing a reactivity. Further preferred $M^1$ is methyl, and further preferred $M^2$ or $M^3$ is hydrogen. In group (P-5), $n^1$ is 1, 2, 3 or 4. Preferred n is 1 or 2 for increasing the reactivity. Further preferred $n^1$ is 1.

When both $P^1$ and $P^3$ are group (P-2), at least one of $Sp^1$ and $Sp^3$ is alkylene in which at least one of —$CH_2$— is replaced by —O—, —COO—, —OCO— or —OCOO—. More specifically, a case where both $P^1$ and $P^3$ are alkenyl such as 1-propenyl is excluded.

$Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine. When hydrogen is replaced by —C≡N, an amount of carbon of the alkylene subjected to replacement by cyano is preferably less than 10. Preferred $Sp^1$, $Sp^2$ or $Sp^3$ is a single bond.

Ring E and ring G are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Preferred ring E or ring G is phenyl. Ring F is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Particularly preferred ring F is 1,4-phenylene or 2-fluoro-1,4-phenylene.

$Z^7$ and $Z^8$ are independently a single bond or alkylene having 1 to 10 carbons, and in the alkylene, at least one of —$CH_2$— may be replaced by —O—, —CO—, —COO— or —OCO—, and at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine. Preferred $Z^7$ or $Z^8$ is a single bond, —$CH_2CH_2$—, —$CH_2O$—, —$OCH_2$—, —COO— or —OCO—. Further preferred $Z^7$ or $Z^8$ is a single bond.

Then, g is 0, 1 or 2. Preferred g is 0 or 1. Then, h, j and k are independently 0, 1, 2, 3 or 4, and a sum of h, j and k is 1 or more. Preferred h, j or k is 1 or 2.

Fifth, the preferred component compounds will be described. Preferred compound (1) includes compound (1-1) to compound (1-3) described above. In the compounds, at least one of the first component preferably includes compound (1-1) or compound (1-2). At least two of the first components preferably includes a combination of compound (1-1) and compound (1-2). Further Preferred compound (1) includes compound (1-1-1) to compound (1-2-2) described above. At least one of the first component preferably includes compound (1-1-1), compound (1-1-2), compound (1-2-1) or compound (1-2-2). At least two of the first components preferably includes a combination of compound (1-1-1) and compound (1-1-2).

Preferred compound (2) includes compound (2-1) to compound (2-27) described above. In the compounds, at least one of the second component preferably includes compound (2-5), compound (2-11), compound (2-12), compound (2-13), compound (2-15), compound (2-16), compound (2-20), compound (2-23) or compound (2-25). At least two of the second components preferably includes a combination of compound (2-12) and compound (2-23), a combination of compound (2-13) and compound (2-16), a combination of compound (2-15) and compound (2-16), a combination of compound (2-16) and compound (2-25) or a combination of compound (2-23) and compound (2-25).

Preferred compound (3) includes compound (3-1) to compound (3-13) described above. In the compounds, at least one of the third component preferably includes compound (3-1), compound (3-3), compound (3-5), compound (3-6), compound (3-7) or compound (3-8). At least two of the third components preferably includes a combination of compound (3-1) and compound (3-3), a combination of compound (3-1) and compound (3-5) or a combination of compound (3-1) and compound (3-6).

Preferred compound (4) includes compound (4-1) to compound (4-27) described above. In the compounds, at least one of the additive component preferably includes compound (4-1), compound (4-2), compound (4-24), compound (4-25), compound (4-26) or compound (4-27). At least two of the additive components preferably includes a combination of compound (4-1) and compound (4-2), a combination of compound (4-1) and compound (4-18), a combination of compound (4-2) and compound (4-24), a combination of compound (4-2) and compound (4-25), a combination of compound (4-2) and compound (4-26), a combination of compound (4-25) and compound (4-26) or a combination of compound (4-18) and compound (4-24). In group (P-1) to group (P-3), preferred $M^1$, $M^2$ or $M^3$ is hydrogen or methyl. Preferred $Sp^1$, $Sp^2$ or $Sp^3$ is a single bond, —$CH_2CH_2$—, —$CH_2O$—, —$OCH_2$—, —COO—, —OCO—, —CO—CH=CH— or —CH=CH—CO—.

Sixth, the additive that may be added to the composition will be described. Such an additive includes the optically active compound, the antioxidant, the ultraviolet light absorber, the dye, the antifoaming agent, the polymerizable compound, the polymerization initiator, the polymerization inhibitor or the like. The optically active compound is added to the composition for inducing a helical structure in a liquid crystal to give a twist angle. Examples of such a compound include compound (5-1) to compound (5-5). A preferred ratio of the optically active compound is about 5% by weight or less. A further preferred ratio is in the range of about 0.01% by weight to about 2% by weight.

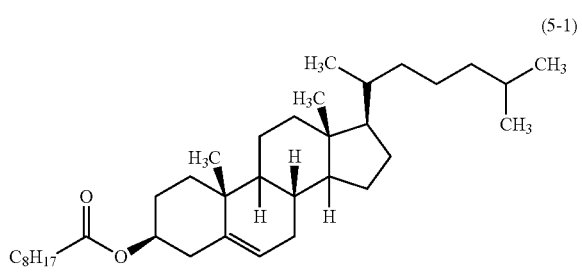

(5-1)

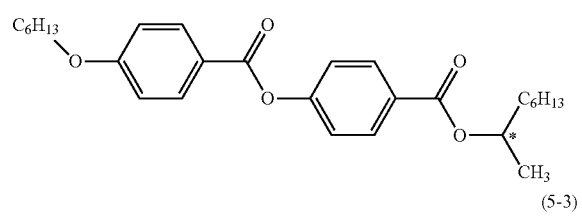

(5-2)

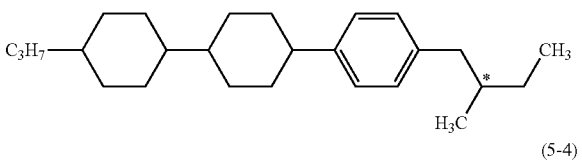

(5-3)

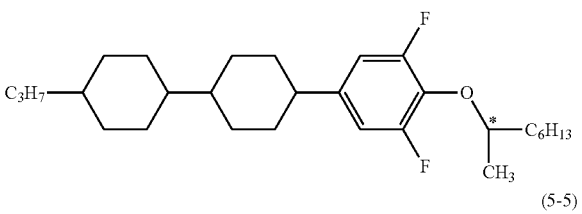

(5-4)

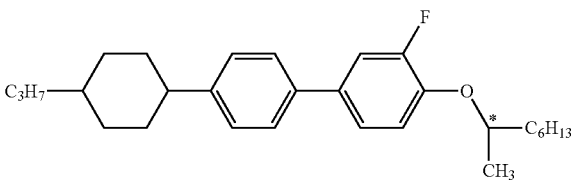

(5-5)

The antioxidant is added to the composition for preventing a decrease in the specific resistance caused by heating in air, or for maintaining a large voltage holding ratio at room temperature and also at the temperature close to the maximum temperature after the device has been used for a long period of time. Preferred examples of the antioxidant include compound (6) where t is an integer from 1 to 9 or the like.

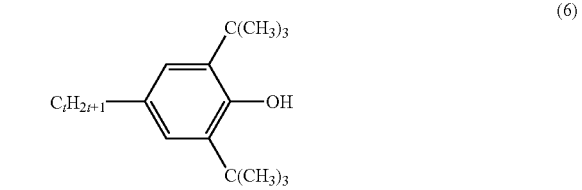

(6)

In compound (6), preferred t is 1, 3, 5, 7 or 9. Further preferred t is 1 or 7. Compound (6) where t is 1 is effective for preventing the decrease in the specific resistance caused by heating in air because the compound (6) has a large volatility. Compound (6) where t is 7 is effective for maintaining the large voltage holding ratio at room temperature and also at the temperature close to the maximum temperature even after the device has been used for a long period of time because the compound (6) has a small volatility. A preferred ratio of the antioxidant is about 50 ppm or more for achieving an effect thereof, and about 600 ppm or less for avoiding a decrease in the maximum temperature or an increase in the minimum temperature. A further preferred ratio is in the range of about 100 ppm to about 300 ppm.

Preferred examples of the ultraviolet light absorber include a benzophenone derivative, a benzoate derivative and a triazole derivative. A light stabilizer such as an amine having steric hindrance is also preferred. A preferred ratio of the absorber or the stabilizer is about 50 ppm or more for achieving an effect thereof, and about 10,000 ppm or less for avoiding the decrease in the maximum temperature or avoiding the increase in the minimum temperature. A further preferred ratio is in the range of about 100 ppm to about 10,000 ppm.

A dichroic dye such as an azo dye or an anthraquinone dye is added to the composition for the purpose of adapting the composition to a device having a guest host (GH) mode. A preferred ratio of the dye is in the range of about 0.01% by weight to about 10% by weight. The antifoaming agent such as dimethyl silicone oil or methyl phenyl silicone oil is added to the composition for preventing foam formation. A preferred ratio of the antifoaming agent is about 1 ppm or more for achieving an effect thereof, and about 1,000 ppm or less for avoiding a poor display. A further preferred ratio is in the range of about 1 ppm to about 500 ppm.

The polymerizable compound is added to the composition for the purpose of adapting the composition to a device having the polymer sustained alignment (PSA) mode. Preferred examples of polymerizable compounds include a compound having a polymerizable group such as acrylate, methacrylate, a vinyl compound, a vinyloxy compound, propenyl ether, an epoxy compound (oxirane, oxetane) and vinyl ketone. Further preferred examples include an acrylate derivative or a methacrylate derivative. A preferred ratio of the polymerizable compound is about 0.05% by weight or more for achieving an effect thereof, and about 10% or less for avoiding a poor display. A further preferred ratio is in the range of about 0.1% by weight to about 2% by weight. The polymerizable compound is polymerized by irradiation with ultraviolet light. The polymerizable compound may be polymerized in the presence of an initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocure 1173 (registered trademark; BASF), each being a photoinitiator, is suitable for radical polymerization. A preferred ratio of the photopolymerization initiator is in the range of about 0.1% by weight to about 5% by weight based on the total weight of the polymerizable compound. A further preferred ratio is in the range of about 1% by weight to about 3% by weight based thereon.

Upon storing the polymerizable compound, the polymerization inhibitor may be added thereto for preventing polymerization. The polymerizable compound is ordinarily added to the composition without removing the polymerization inhibitor. Examples of the polymerization inhibitor include hydroquinone and a hydroquinone derivative such as methylhydroquinone, 4-tert-butylcatechol, 4-methoxyphenol or phenothiazine.

Seventh, the methods for synthesizing the component compounds will be described. The compounds can be prepared according to known methods. Examples of the synthetic methods are described. Compound (2-3) and compound (2-8) are prepared by a method described in JP H2-233626 A. Compound (3-1) is prepared by a method described in JP S59-176221 A. Compound (3-13) is prepared by a method described in JP H2-237949 A. The antioxidant is commercially available. A compound where t in formula (6) is 1 can be obtained from Sigma-Aldrich Corporation. A compound where t in compound (6) is 7 or the like can be prepared according to a method described in U.S. Pat. No. 3,660,505 B.

Any compounds whose synthetic methods are not described can be prepared according to methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition of the invention mainly has a minimum temperature of about −10° C. or lower, a maximum temperature of about 70° C. or higher, and an optical anisotropy in the range of about 0.07 to about 0.20. A device including the composition has the large voltage holding ratio. The composition is suitable for use in the AM device. The composition is particularly suitable for use in a transmissive AM device. The composition having an optical anisotropy in the range of about 0.08 to about 0.25 may be prepared by controlling the ratio of the component compounds or by mixing any other liquid crystal compound, and further the composition having an optical anisotropy in the range of about 0.10 to about 0.30 may be prepared. The composition can be used as the composition having the nematic phase, and as the optically active composition by adding the optically active compound.

The composition can be used for the AM device. The composition can also be used for a PM device. The composition can also be used for the AM device and the PM device each having a mode such as the PC mode, the TN mode, the STN mode, the ECB mode, the OCB mode, the IPS mode, the FFS mode, the VA mode and the FPA mode. Use for the AM device having the TN mode, the OCB mode, the IPS mode or the FFS mode is particularly preferred. In the AM device having the IPS mode or the FFS mode, alignment of liquid crystal molecules when no voltage is applied may be parallel or vertical to a glass substrate. The device may be of a reflective type, a transmissive type or a transflective type. Use for the transmissive device is preferred. Use for an amorphous silicon-TFT device or a polycrystal silicon-TFT device is allowed. The composition can also be used for a nematic curvilinear aligned phase (NCAP) device prepared by microencapsulating the composition, or for a polymer dispersed (PD) device in which a three-dimensional network-polymer is formed in the composition.

EXAMPLES

The invention will be described in greater detail by way of Examples. However, the invention is not limited by the Examples. The invention includes a mixture of a composition in Example M1 and a composition in Example M2. The invention also includes a mixture in which at least two compositions in Examples are mixed. The thus prepared compound was identified by methods such as an NMR analysis. Characteristics of the compound and the composition were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane (TMS) was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: GC-14B Gas Chromatograph made by Shimadzu Corporation was used for measurement. A carrier gas was helium (2 mL/per minute). A sample injector and a detector (FID) were set to 280° C. and 300° C., respectively. A capillary column DB-1 (length 30 m, bore 0.32 mm, film thickness 0.25 µm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating component compounds: HP-1 (length 30 m, bore 0.32 mm, film thickness 0.25 µm) made by Agilent Technologies, Inc., Rtx-1 (length 30 m, bore 0.32 mm, film thickness 0.25 µm) made by Restek Corporation and BP-1 (length 30 m, bore 0.32 mm, film thickness 0.25 µm) made by SGE International Pty. Ltd. A capillary column CBP1-M50-025 (length 50 m, bore 0.25 mm, film thickness 0.25 µm) made by Shimadzu Corporation may also be used for the purpose of avoiding an overlap of peaks of the compounds.

A ratio of liquid crystal compounds contained in the composition may be calculated by the method as described below. The mixture of liquid crystal compounds is detected by gas chromatograph (FID). An area ratio of each peak in the gas chromatogram corresponds to the ratio (weight ratio) of the liquid crystal compound. When the capillary columns described above were used, a correction coefficient of each of the liquid crystal compounds may be regarded as 1 (one). Accordingly, the ratio (% by weight) of the liquid crystal compound is calculated from the area ratio of each peak.

Sample for measurement: When characteristics of a composition was measured, the composition was used as a sample as was. Upon measuring characteristics of a compound, a sample for measurement was prepared by mixing the compound (15% by weight) with a base liquid crystal (85% by weight). Values of characteristics of the compound were calculated, according to an extrapolation method, using values obtained by measurement. (Extrapolated value)={(measured value of a sample for measurement)−0.85×(measured value of abase liquid crystal)}/0.15. When a smectic phase (or crystals) precipitates at the ratio thereof at 25° C., a ratio of the compound to the base liquid crystal was changed step by step in the order of (10% by weight:90% by weight), (5% by weight:95% by weight) and (1% by weight: 99% by weight). Values of maximum temperature, optical anisotropy, viscosity and dielectric anisotropy with regard to the compound were determined according to the extrapolation method.

A base liquid crystal described below was used. A ratio of the component compound was expressed in terms of weight percent (% by weight).

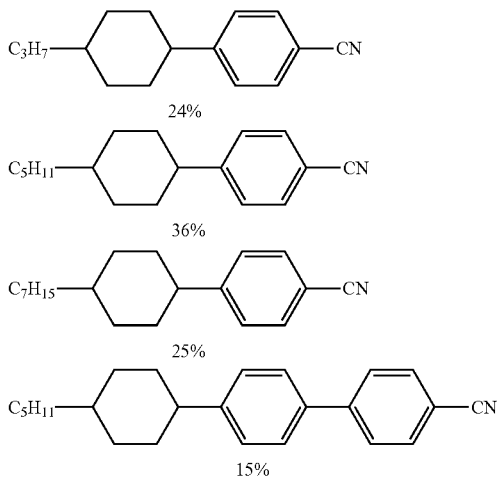

Measuring method: Measurement of characteristics was carried out by the methods described below. Most of the measuring methods are applied as described in the Standard of the Japan Electronics and Information Technology Industries Association (hereinafter abbreviated as JEITA) (JEITA EIAJ ED-2521B) discussed and established by JEITA, or modified thereon. No thin film transistor (TFT) was attached to a TN device used for measurement.

(1) Maximum temperature of nematic phase (NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured.

(2) Minimum temperature of nematic phase ($T_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc of the sample was expressed as $T_c$<−20° C.

(3) Viscosity (bulk viscosity; η; measured at 20° C.; mPa·S): A cone-plate (E type) rotational viscometer made by Tokyo Keiki, Inc. was used for measurement.

(4) Viscosity (rotational viscosity; γ1; measured at 25° C.; mPa·S): Measurement was carried out according to a method described in M. Imai et al., Molecular Crystals and Liquid Crystals, Vol. 259, p. 37 (1995). A sample was put in a TN device in which a twist angle was 0 degree and a distance (cell gap) between two glass substrates was 5 micrometers. Voltage was applied stepwise to the device in the range of 16 V to 19.5 V at an increment of 0.5 V. After a period of 0.2 second with no voltage application, voltage was applied repeatedly under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) described on page 40 of the paper presented by M. Imai et al. A value of a dielectric anisotropy required for the calculation was determined using the device by which the rotational viscosity was measured and by the method described below.

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy was calculated from an equation: Δn=n∥−n⊥.

(6) Dielectric anisotropy (Δ∈; measured at 25° C.): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in a major axis direction of the liquid crystal molecules was measured. Sine waves (0.5 V, 1 kHz) were applied to the device, and after 2 seconds, a dielectric constant (∈⊥) in a minor axis direction of the liquid crystal molecules was measured. A value of dielectric anisotropy was calculated from an equation: Δ∈=∈∥−∈⊥.

(7) Threshold voltage (Vth; measured at 25° C.; V): An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(8) Voltage holding ratio (VHR-1; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (60 microseconds at 1 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage holding ratio (VHR-2; measured at 80° C.; %): A voltage holding ratio was measured according to procedures identical with the procedures described above except that measurement was carried out at 80° C. in place of 25° C. The thus obtained value was expressed in terms of VHR-2.

(10) Voltage holding ratio (VHR-3; measured at 25° C.; %): Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with light for 20 minutes. A light source was an ultra high-pressure mercury lamp USH-500 D (made by Ushio, Inc.), and a distance between the device and the light source was 20 centimeters. In measurement of VHR-3, a decaying voltage was measured for 16.7 milliseconds. A composition having large VHR-3 has a large stability to ultraviolet light. A value of VHR-3 is preferably 90% or more, and further preferably, 95% or more.

(11) Voltage holding ratio (VHR-4; measured at 60° C.; %): Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with light for 67 minutes. A light source was black light (peak wavelength of 369 nm), and a distance between the device and the light source was 5 millimeters. In measurement of VHR-4, a decaying voltage was measured for 166.7 milliseconds. A composition having large VHR-4 has a large stability to ultraviolet light.

(12) Voltage holding ratio (VHR-5; measured at 25° C.; %): Stability to heat was evaluated by measuring a voltage holding ratio after a TN device into which a sample was injected was heated in a constant-temperature bath at 80° C. for 500 hours. In measurement of VHR-4, a decaying voltage was measured for 16.7 milliseconds. A composition having large VHR-4 has a large stability to heat.

(13) Response time (τ; measured at 25° C.; ms): An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured, in which the maximum amount of light corresponds to 100% transmittance, and the minimum amount of light corresponds to 0% transmittance. A rise time (τr; millisecond) was expressed in terms of time required for a change from 90% transmittance to 10% transmittance. A fall time (τf; millisecond) was expressed in terms of time required for a change from 90% transmittance to 10% transmittance. A response time was represented by a sum of the rise time and the fall time thus obtained.

(14) Elastic constant (K; measured at 25° C.; pN): HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of K11 and K33 were obtained from equation (2.99). Next, K22 was calculated using the previously determined values of K11 and K33 in formula (3.18) on page 171. Elastic constant K was expressed in terms of a mean value of the thus determined K11, K22 and K33.

(15) Specific resistance (ρ; measured at 25 C; Ωcm): Into a vessel equipped with electrodes, 1.0 mL of a sample was injected. A direct current voltage (10 V) was applied to the vessel, and a direct current after 10 seconds was measured. Specific resistance was calculated from the following equation:

(specific resistance)={(voltage)×(electric capacity of the vessel)}/{(direct current)×(dielectric constant of vacuum)}.

(16) Helical pitch (P; measured at room temperature; μm): A helical pitch was measured according to a wedge method. Refer to page 196 in "Handbook of Liquid Crystals (Ekisho Binran in Japanese)" (issued in 2000, Maruzen Co., Ltd.). A sample was injected into a wedge cell and left to stand at room temperature for 2 hours, and then a gap (d2−d1) between disclination lines was observed by a polarizing microscope (trade name: MM40/60 Series, Nikon Corporation). A helical pitch (P) was calculated according to the following equation in which an angle of the wedge cell was expressed as θ:

$$P = 2 \times (d2-d1) \times \tan\theta.$$

The compounds described in Examples were described using symbols according to definitions in Table 3 below. In Table 3, the configuration of 1,4-cyclohexylene is trans. A parenthesized number next to a symbolized compound in Examples corresponds to the number of the compound. A symbol (—) means any other liquid crystal compound. A ratio (percentage) of the liquid crystal compound is expressed in terms of weight percent (% by weight) based on the weight of the liquid crystal composition. Values of the characteristics of the composition were summarized in the last part.

TABLE 3

| Method for Description of Compounds using Symbols R—($A_1$)—$Z_1$— - - - —$Z_n$—($A_n$)—R' | |
|---|---|
| 1) Left-terminal Group R— | Symbol |
| $C_nH_{2n+1}$— | n- |
| $C_nH_{2n+1}O$— | nO— |
| $C_mH_{2m+1}OC_nH_{2n}$— | mOn- |
| $CH_2=CH$— | V— |
| $C_nH_{2n+1}$—CH=CH— | nV— |
| $CH_2=CH$—$C_nH_{2n}$— | Vn- |
| $C_mH_{2m+1}$—CH=CH—$C_nH_{2n}$— | mVn- |
| $CF_2=CH$— | VFF— |
| $CF_2=CH$—$C_nH_{2n}$— | VFFn- |
| 2) Right-terminal Group —R' | Symbol |
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —$C_nH_{2n}$—CH=CH—$C_mH_{2m+1}$ | -nVm |
| —CH=$CF_2$ | —VFF |
| —$COOCH_3$ | —EMe |
| —F | —F |
| —Cl | —CL |
| —$OCF_3$ | —$OCF_3$ |
| —$CF_3$ | —$CF_3$ |
| —CN | —C |
| —CF=CH—$CF_3$ | —FVCF3 |

TABLE 3-continued

| 3) Bonding Group —$Z_n$— | Symbol |
|---|---|
| —$C_2H_4$— | 2 |
| —COO— | E |
| —CH=CH— | V |
| —C≡C— | T |
| —$CF_2O$— | X |
| —$CH_2O$— | 1O |

| 4) Ring Structure —$A_n$— | Symbol |
|---|---|
| (cyclohexane) | H |
| (tetrahydropyran, O top) | Dh |
| (tetrahydropyran, O side) | dh |
| (phenyl) | B |
| (3-fluorophenyl) | B(F) |
| (2-fluorophenyl) | B(2F) |
| (3,5-difluorophenyl) | B(F,F) |
| (2,5-difluorophenyl) | B(2F,5F) |
| (1,3-dioxane) | G |
| (pyrimidine) | Py |
| (cyclohexadiene) | Bm |

TABLE 3-continued

5) Examples of Description

Example 1. 3-HH—V1

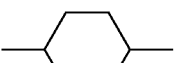

Example 2. 3-BB(F)B(F,F)—F

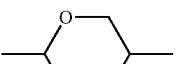

Example 3. 4-BB(F)B(F,F)XB(F,F)—F

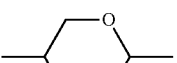

Example 4. 5-BB(2F)BBm-2

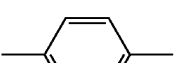

Example 1

Synthesis of Compound (1-1-1)

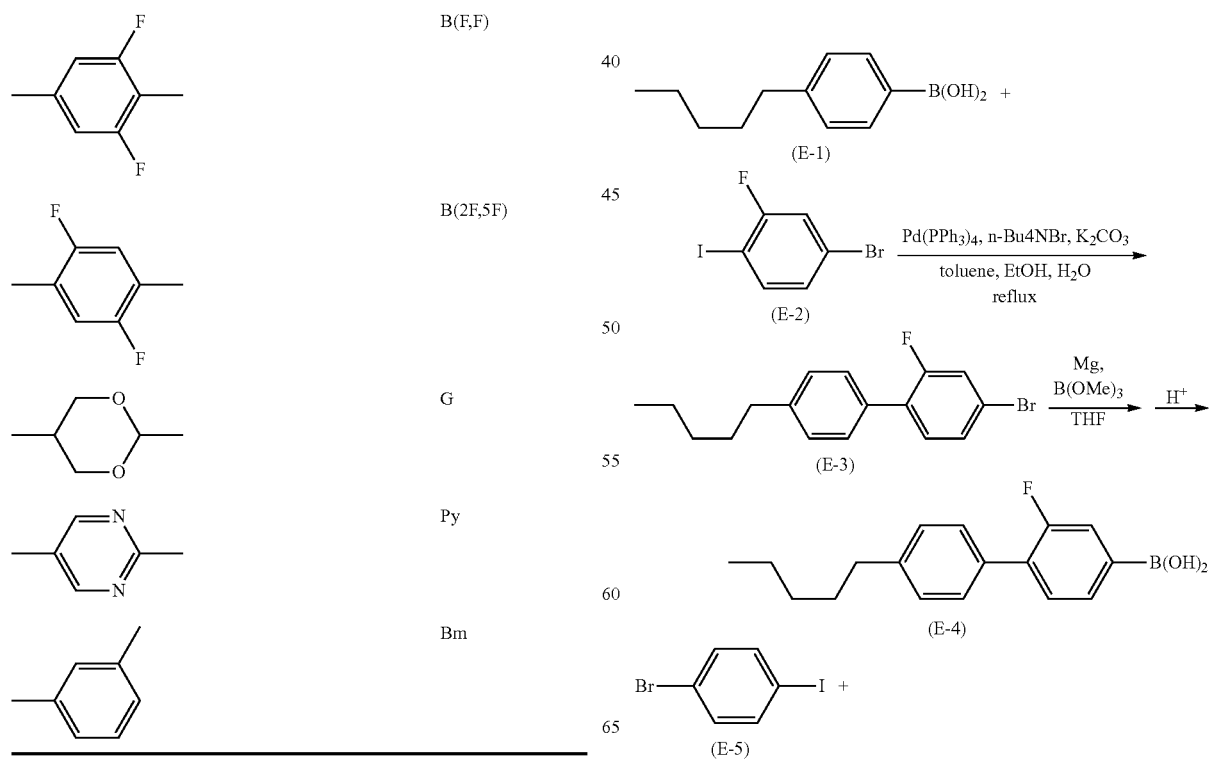

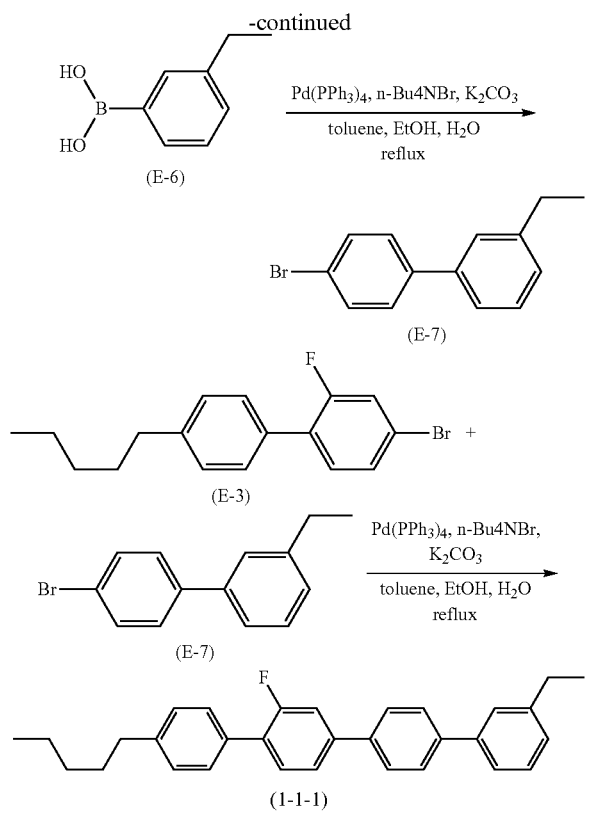

First Step

In a reaction vessel under a nitrogen atmosphere, (4-pentylphenyl)boronic acid (E-1) (26.8 g, 139.58 mmol), 4-bromo-2-fluoro-1-iodobenzene(E-2) (40.0 g, 132.94 mmol), tetrakistriphenyl phosphine palladium (1.54 g, 1.33 mmol), potassium carbonate (27.6 g, 199.41 mmol) and tetrabutylammonium bromide (10.71 g, 33.23 mmol) were put into a mixed solvent of 200 mL of toluene, 50 mL of ethanol and 200 mL of water, and the resulting mixture was refluxed for 8 hours. The resulting reaction mixture was subjected to extraction with toluene. A combined organic layer was washed with water and saturated brine, and dried over magnesium sulfate, and then a solvent was distilled off using an evaporator. The resulting residue was purified by silica gel column chromatography and recrystallized to give 4-bromo-2-fluoro-4'-pentyl-1,1'-biphenyl (E-3) (35.1 g, yield: 78.3%).

Second Step

In a reaction vessel under a nitrogen atmosphere, to a THF (50 mL) suspension of magnesium (2.92 g, 120.20 mmol), a THF (200 mL) solution of compound (E-3) (35.1 g, 109.27 mmol) obtained in the first step was added dropwise at 50° C. or lower. The resulting reaction mixture was stirred at room temperature for 1 hour, and then cooled down to −60° C. or lower, and a THF solution (100 mL) of trimethyl borate (13.6 g, 131.12 mmol) was added dropwise thereto. The resulting reaction mixture was returned to room temperature, and quenched using 3 N hydrochloric acid, and then subjected to extraction with toluene. A combined organic layer was washed with water and saturated brine, and dried over magnesium sulfate, and then a solvent was distilled off using an evaporator. The resulting residue was washed with heptane to give (2-fluoro-4'-pentyl-[1,1'-biphenyl]-4-yl)boronic acid (E-4) (21.4 g, yield: 68.4%).

Third Step

In a reaction vessel under a nitrogen atmosphere, 1-bromo-4-iodobenzene (E-5) (19.6 g, 69.10 mmol), 3-ethylphenylboronic acid (E-6) (11.4 g, 76.01 mmol), tetrakistriphenyl phosphine palladium (2.4 g, 2.07 mmol), potassium carbonate (14.3 g, 103.65 mmol) and tetrabutylammonium bromide (5.57 g, 17.27 mmol) were put into a mixed solvent of 100 mL of toluene, 20 mL of ethanol and 100 mL of water, and the resulting mixture was refluxed for 8 hours. The resulting reaction mixture was subjected to extraction with toluene. A combined organic layer was washed with water and saturated brine, and dried over magnesium sulfate, and then a solvent was distilled off using an evaporator. A residue was purified by silica gel column chromatography to give 4'-bromo-3-ethyl-1,1'-biphenyl(E-7) (15.5 g, yield: 83.5%).

Fourth Step

In a reaction vessel under a nitrogen atmosphere, put compound (E-4) (15.9 g, 55.52 mmol) obtained in the second step, compound (E-7) (14.5 g, 55.52 mmol) obtained in the third step, tetrakistriphenyl phosphine palladium (0.64 g, 0.55 mmol), potassium carbonate (11.5 g, 83.28 mmol) and tetrabutylammonium bromide (4.47 g, 13.88 mmol) into a mixed solvent of 100 mL of toluene, 20 mL of ethanol and 100 mL of water, and refluxed for 8 hours. A reaction mixture was subjected to extraction with toluene. A combined organic layer was washed with water and saturated brine, and dried over magnesium sulfate, and then a solvent was distilled off using an evaporator. The resulting residue was purified by silica gel column chromatography and recrystallized to give compound (1-1-1) (17.4 g, yield: 74.2%).

$^1$H-NMR (CDCl$_3$) δ: 7.71-7.67 (m, 4H), 7.55-7.36 (m, 8H), 7.30-7.26 (m, 2H), 7.24-7.20 (m, 1H), 2.72 (q, 2H), 2.66 (t, 2H), 1.67 (tt, 2H), 1.40-1.34 (m, 4H), 1.31 (t, 3H), 0.92 (t, 3H).

A liquid crystal composition was prepared from 10% by weight of compound (1-1-1) and 90% by weight of a base liquid crystal. Characteristics of the resulting liquid crystal composition were measured, and the characteristics of compound (1-1-1) were calculated by extrapolating the measured values. The results were as described below.

Maximum temperature (NI)=132.7° C.; dielectric anisotropy (Δ∈)=5.1; optical anisotropy (Δn)=0.287; viscosity (η)=92.7 mPa·s.

Example 2 and Comparative Example 1

(Comparison of Solubility in a Liquid Crystal Composition)

Compound (1-1-1) was added to a base liquid crystal at a ratio of 10% by weight, and heated at 100° C. for 10 minutes. The resulting solution was allowed to stand for two days at room temperature. Then, whether or not crystals were precipitated was observed by visual observation. Meanwhile, compound (R-1) described below was also observed in a similar manner. The results are shown in Table 4. In Table 4, "good" represents no precipitation of crystals, and "poor" represents occurrence of precipitation. Table 4 shows that the compound of the invention has a good solubility in the base liquid crystal.

(R-1)

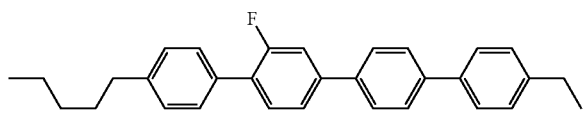

TABLE 4

Comparison of solubility in a liquid crystal composition

| Compound | Structural formula | Solubility (two days at room temperature) |
|---|---|---|
| (1-1-1) | | Good |
| (R-1) | | Poor |

Example M1

| 5-BB(2F)BBm-2 | (1-1-1) | 0.5% |
| 3-HHXB(F,F)-F | (2-5) | 9.0% |
| 4-GHB(F,F)-F | (2-7) | 5.0% |
| 2-HHBB(F,F)-F | (2-17) | 4.0% |
| 3-HHBB(F,F)-F | (2-17) | 6.0% |
| 4-HHBB(F,F)-F | (2-17) | 5.0% |
| 4-GB(F)B(F,F)XB(F,F)-F | (2-23) | 7.0% |
| 4-BB(F)B(F,F)XB(F,F)-F | (2-25) | 9.0% |
| 5-BB(F)B(F,F)XB(F,F)-F | (2-25) | 7.0% |
| 3-HHB-CL | (2) | 3.0% |
| 3-HH-V | (3-1) | 29.0% |
| 3-HH-VFF | (3-1) | 4.0% |
| 3-HB-O2 | (3-2) | 3.0% |
| 3-HHB-3 | (3-5) | 3.0% |
| 5-HBB-2 | (3-6) | 2.5% |
| 3-HBBH-1O1 | (—) | 3.0% |

A composition having positive dielectric anisotropy was prepared, and characteristics thereof were measured.

NI=107.1° C.; $T_c$<−20° C.; Δn=0.114; Δ∈=11.0; Vth=1.48 V; η=16.4 mPa·s; VHR-4=51.3%.

Comparative Example M1

A composition containing no compound (1-1-1) was prepared. In the composition in Example M1, 15 kinds of compounds from which compound (1-1-1) was excluded were mixed at a same ratio. Characteristics of the composition were measured.

NI=107.2° C.; $T_c$<−20° C.; Δn=0.113; Δ∈=11.0; Vth=1.48 V; η=16.0 mPa·s; VHR-4=34.3%.

A voltage holding ratio (VHR-4) of the composition after irradiation with ultraviolet light in Example M1 was 51.3%, and a voltage holding ratio of the composition in Comparative Example M1 was 34.3%. From the results, a TN device in Example M1 was found to have a larger voltage holding ratio in comparison with the device in Comparative Example M1.

Example M2

| 5-BB(2F)B(2F)Bm-2 | (1-1-2) | 0.3% |
| 5-HBB(2F)B(2F)Bm-2 | (1-2-2) | 0.3% |
| 3-HHXB(F,F)-F | (2-5) | 9.0% |
| 4-GHB(F,F)-F | (2-7) | 5.0% |
| 2-HHBB(F,F)-F | (2-17) | 4.0% |
| 3-HHBB(F,F)-F | (2-17) | 6.0% |
| 4-HHBB(F,F)-F | (2-17) | 5.0% |
| 4-GB(F)B(F,F)XB(F,F)-F | (2-23) | 7.0% |
| 4-BB(F)B(F,F)XB(F,F)-F | (2-25) | 9.0% |
| 5-BB(F)B(F,F)XB(F,F)-F | (2-25) | 7.0% |
| 3-HHB-CL | (2) | 3.0% |
| 3-HH-V | (3-1) | 29.0% |
| 3-HH-VFF | (3-1) | 4.0% |
| 3-HB-O2 | (3-2) | 3.0% |
| 3-HHB-3 | (3-5) | 3.0% |
| 5-HBB-2 | (3-6) | 2.4% |
| 3-HBBH-1O1 | (—) | 3.0% |

A composition having positive dielectric anisotropy was prepared, and characteristics thereof were measured.

NI=109.3° C.; $T_c$<−20° C.; Δn=0.113; Δ∈=10.4; Vth=1.59 V; η=15.9 mPa·s; VHR-4=52.1%.

Example M3

| 5-B(F)BB(2F)Bm-2 | (1-1-3) | 1.0% |
| 3-HHXB(F,F)-F | (2-5) | 11.0% |
| 3-HGB(F,F)-F | (2-6) | 3.0% |
| 4-GHB(F,F)-F | (2-7) | 10.0% |
| 3-BB(F,F)XB(F,F)-F | (2-16) | 9.0% |
| 2-HHBB(F,F)-F | (2-17) | 4.0% |
| 3-HHBB(F,F)-F | (2-17) | 5.0% |
| 4-HHBB(F,F)-F | (2-17) | 5.0% |
| 5-HHBB(F,F)-F | (2-17) | 5.0% |
| 4-BB(F)B(F,F)XB(F,F)-F | (2-25) | 9.0% |
| 5-BB(F)B(F,F)XB(F,F)-F | (2-25) | 3.0% |
| 3-HH-V | (3-1) | 20.0% |
| 3-HH-V1 | (3-1) | 5.0% |
| 3-HHB-1 | (3-5) | 8.0% |
| 3-HBB-2 | (3-6) | 2.0% |

A composition having positive dielectric anisotropy was prepared, and characteristics thereof were measured.

NI=106.6° C.; $T_c$<−20° C.; Δn=0.110; Δ∈=11.3; Vth=1.50 V; η=20.8 mPa·s; VHR-4=54.0%.

Example M4

| | | |
|---|---|---|
| 5-BB(2F,5F)BBm-2 | (1-1-4) | 0.5% |
| 3-HHB(F,F)-F | (2-3) | 3.0% |
| 3-HHXB(F,F)-F | (2-5) | 13.0% |
| 3-HB(F)B(F,F)-F | (2-9) | 5.0% |
| 3-BB(F,F)XB(F,F)-F | (2-16) | 16.0% |
| 3-HHBB(F,F)-F | (2-17) | 3.0% |
| 4-GBB(F)B(F,F)-F | (2-19) | 3.0% |
| 3-HBBXB(F,F)-F | (2-20) | 8.0% |
| 3-HBB(F,F)XB(F,F)-F | (2-21) | 6.0% |
| 3-HH-V | (3-1) | 24.0% |
| 3-HH-V1 | (3-1) | 7.0% |
| V2-BB-1 | (3-3) | 3.0% |
| 3-HHEH-3 | (3-4) | 3.0% |
| 1-BB(F)B-2V | (3-8) | 3.0% |
| 5-HBB(F)B-2 | (3-13) | 2.5% |

A composition having positive dielectric anisotropy was prepared, and characteristics thereof were measured.

NI=84.5° C.; $T_c$<−20° C.; Δn=0.109; Δ∈=8.5; Vth=1.45 V; η=17.2 mPa·s; VHR-4=50.9%.

Example M5

| | | |
|---|---|---|
| 5-BB(2F,5F)B(2F)Bm-2 | (1-1-5) | 0.5% |
| 3-HB-CL | (2-1) | 6.0% |
| 5-HXB(F,F)-F | (2-2) | 5.0% |
| 3-HHB(F,F)-F | (2-3) | 10.0% |
| 3-HHEB(F,F)-F | (2-4) | 9.0% |
| 3-HHXB(F,F)-F | (2-5) | 19.0% |
| 2-HBEB(F,F)-F | (2-10) | 3.0% |
| 3-HBEB(F,F)-F | (2-10) | 3.0% |
| 3-BBXB(F,F)-F | (2-15) | 3.0% |
| 3-BB(F,F)XB(F,F)-F | (2-16) | 7.0% |
| 3-dhBB(F,F)XB(F,F)-F | (2-22) | 4.0% |
| 3-BB(F)B(F,F)XB(F)B(F,F)-F | (2-27) | 3.0% |
| 3-HH-V | (3-1) | 7.0% |
| 3-HH-V1 | (3-1) | 10.0% |
| 5-HH-V | (3-1) | 7.0% |
| 3-HHEBH-3 | (3-9) | 3.5% |

A composition having positive dielectric anisotropy was prepared, and characteristics thereof were measured.

NI=78.0° C.; $T_c$<−20° C.; Δn=0.086; Δ∈=10.0; Vth=1.09 V; η=17.0 mPa·s; VHR-4=49.5%.

Example M6

| | | |
|---|---|---|
| V2-B(F)B(2F)B(2F)Bm-2 | (1-1-6) | 0.5% |
| 3-GB(F,F)XB(F,F)-F | (2-12) | 4.0% |
| 3-BB(F)B(F,F)-CF3 | (2-14) | 3.0% |
| 3-BB(F,F)XB(F,F)-F | (2-16) | 16.0% |
| 3-HHB(F)B(F,F)-F | (2-18) | 4.0% |
| 3-HBBXB(F,F)-F | (2-20) | 10.0% |
| 4-GB(F)B(F,F)XB(F,F)-F | (2-23) | 4.0% |
| 5-GB(F)B(F,F)XB(F,F)-F | (2-23) | 4.0% |
| 4-BB(F)B(F,F)XB(F,F)-F | (2-25) | 7.0% |
| 3-HH-V | (3-1) | 25.0% |
| 3-HH-O1 | (3-1) | 3.0% |
| 1-BB-3 | (3-3) | 3.0% |
| V-HHB-1 | (3-5) | 11.0% |
| 5-B(F)BB-2 | (3-7) | 2.5% |
| 2-BB(F)B-3 | (3-8) | 3.0% |

A composition having positive dielectric anisotropy was prepared, and characteristics thereof were measured.

NI=74.0° C.; $T_c$<−20° C.; Δn=0.120; Δ∈=12.4; Vth=1.24 V; η=17.8 mPa·s; VHR-4=55.8%.

Example M7

| | | |
|---|---|---|
| 3-B(2F)B(2F)B(2F)Bm-2 | (1-1-7) | 1.2% |
| 3-HBB(F,F)-F | (2-8) | 4.0% |
| 3-GB(F)B(F,F)-F | (2-11) | 3.0% |
| 3-BB(F)B(F,F)-F | (2-13) | 6.0% |
| 3-BB(F,F)XB(F,F)-F | (2-16) | 18.0% |
| 3-HBBXB(F,F)-F | (2-20) | 3.0% |
| 3-BB(F)B(F,F)XB(F,F)-F | (2-25) | 3.0% |
| 4-BB(F)B(F,F)XB(F,F)-F | (2-25) | 7.0% |
| 4-BB(F)XB(F)B(F,F)-F | (2-26) | 3.0% |
| 3-HH-V | (3-1) | 29.0% |
| V-HHB-1 | (3-5) | 11.0% |
| 2-BB(F)B-2V | (3-8) | 2.8% |
| 3-HB(F)HH-5 | (3-10) | 3.0% |
| 5-HBBH-3 | (3-11) | 3.0% |
| 3-HB(F)BH-3 | (3-12) | 3.0% |

A composition having positive dielectric anisotropy was prepared, and characteristics thereof were measured.

NI=80.7° C.; $T_c$<−30° C.; Δn=0.124; Δ∈=9.9; Vth=1.54 V; η=20.6 mPa·s; VHR-4=56.2%.

Example M8

| | | |
|---|---|---|
| 5-HBB(2F)B(2F)Bm-2 | (1-2-2) | 0.5% |
| 3-HHXB(F,F)-F | (2-5) | 10.0% |
| 4-GHB(F,F)-F | (2-7) | 10.0% |
| 3-BB(F,F)XB(F,F)-F | (2-16) | 6.0% |
| 2-HHBB(F,F)-F | (2-17) | 4.0% |
| 3-HHBB(F,F)-F | (2-17) | 6.0% |
| 4-HHBB(F,F)-F | (2-17) | 5.0% |
| 5-HHBB(F,F)-F | (2-17) | 5.0% |
| 3-GBB(F)B(F,F)-F | (2-19) | 3.0% |
| 4-BB(F)B(F,F)XB(F,F)-F | (2-25) | 8.0% |
| 5-BB(F)B(F,F)XB(F,F)-F | (2-25) | 3.0% |
| 3-HH-V | (3-1) | 19.0% |
| 2-HH-3 | (3-1) | 4.0% |
| 3-HH-4 | (3-1) | 3.0% |
| V2-BB-1 | (3-3) | 6.0% |
| 3-HHB-1 | (3-5) | 5.0% |
| 5-HBB(F)B-3 | (3-13) | 2.5% |

A composition having positive dielectric anisotropy was prepared, and characteristics thereof were measured.

NI=106.6° C.; $T_c$<−20° C.; Δn=0.115; Δ∈=10.6; Vth=1.55 V; η=19.4 mPa·s; VHR-4=52.4%.

INDUSTRIAL APPLICABILITY

A liquid crystal composition of the invention satisfies at least one of characteristics such as a high maximum temperature, a low minimum temperature, a small viscosity, a suitable optical anisotropy, a large dielectric anisotropy, a large specific resistance, a large elastic constant, a high stability to ultraviolet light, a high stability to heat and the large elastic constant, or has a suitable balance regarding at least two of the characteristics. A liquid crystal display device including the composition has characteristics such as a short response time, a large voltage holding ratio, a large contrast ratio and a long service life, and thus can be used for a liquid crystal projector, a liquid crystal television and so forth.

What is claimed is:

1. A liquid crystal composition that has a positive dielectric anisotropy, and contains at least one compound selected from the group of compounds represented by formula (1) as a first component:

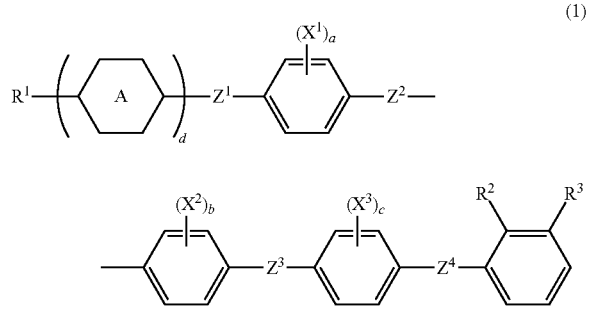

(1)

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, and one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; $Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

2. The liquid crystal composition according to claim 1, containing at least one compound selected from the group of compounds represented by formulas (1-1) to (1-3) as the first component:

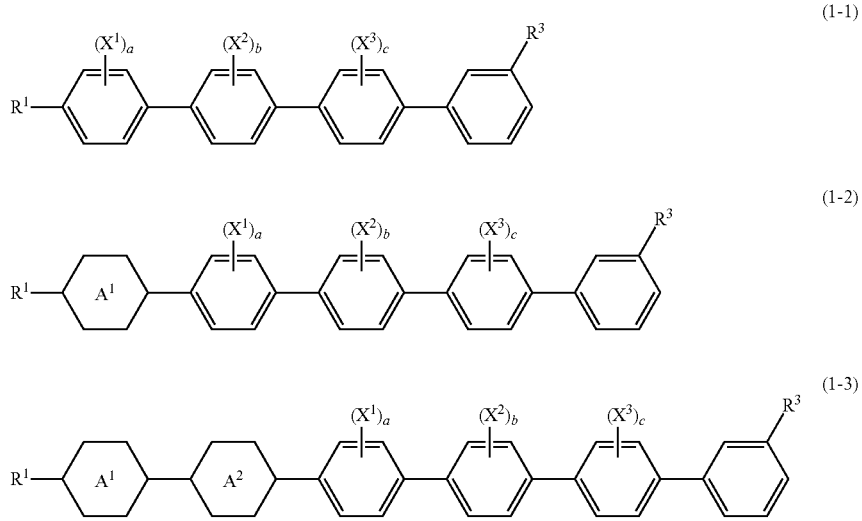

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; and a, b and c are independently 0, 1, 2, 3 or 4.

3. The liquid crystal composition according to claim 1, containing at least one compound selected from the group of compounds represented by formulas (1-1-1) to (1-1-9), formula (1-2-1) and formula (1-2-2) as the first component:

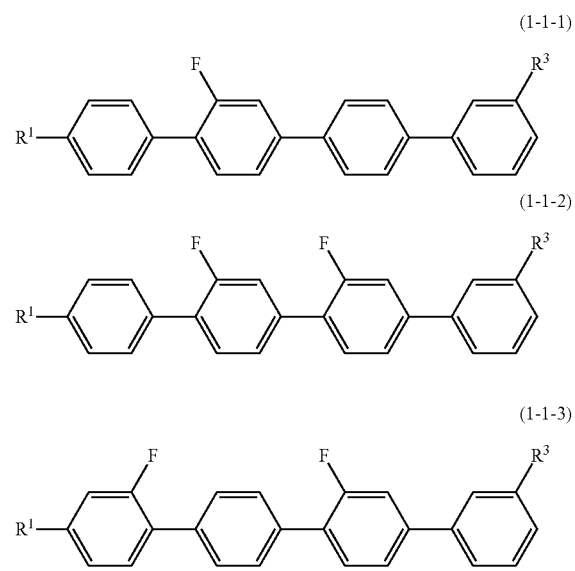

-continued

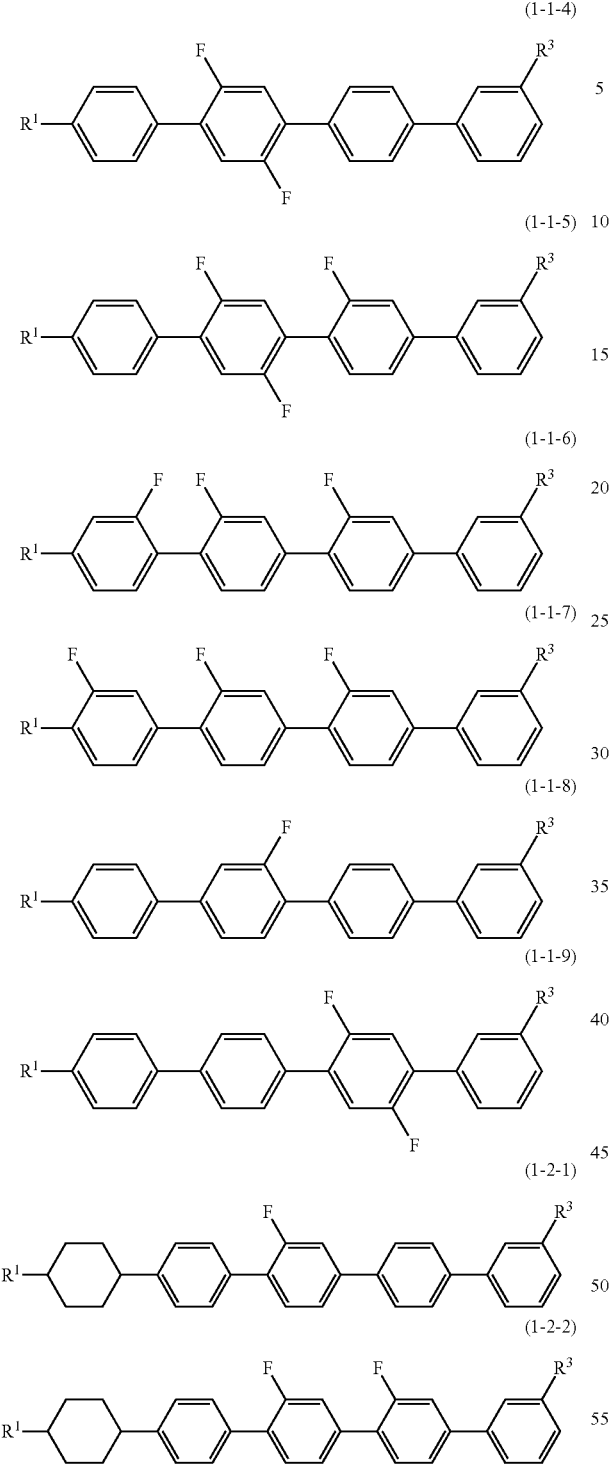

wherein, in formulas (1-1-1) to (1-1-9), formula (1-2-1) and formula (1-2-2), R¹ and R³ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

4. The liquid crystal composition according to claim 1, wherein a ratio of the first component is in the range of 0.03% by weight to 10% by weight based on the weight of the liquid crystal composition.

5. The liquid crystal composition according to claim 1, containing at least one compound selected from the group of compounds represented by formula (2) as a second component:

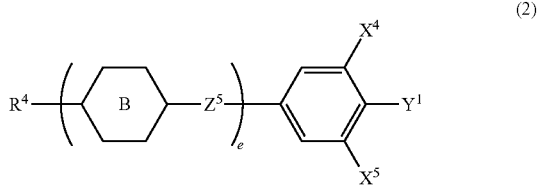

wherein, in formula (2), $R^4$ is alkyl having 1 to 12 carbons, alkoxy having 1 to 12 carbons or alkenyl having 2 to 12 carbons; ring B is 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl or tetrahydropyran-2,5-diyl; $Z^5$ is a single bond, —CH$_2$CH$_2$—, —COO— or —CF$_2$O—; $X^4$ and $X^5$ are independently hydrogen or fluorine; $Y^1$ is fluorine, chlorine, alkyl having 1 to 12 carbons in which at least one of hydrogen is replaced by halogen, alkoxy having 1 to 12 carbons in which at least one of hydrogen is replaced by halogen, or alkenyloxy having 2 to 12 carbons in which at least one of hydrogen is replaced by halogen; and e is 1, 2, 3 or 4.

6. The liquid crystal composition according to claim 5, containing at least one compound selected from the group of compounds represented by formulas (2-1) to (2-27) as the second component:

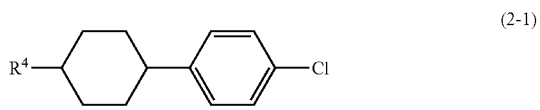

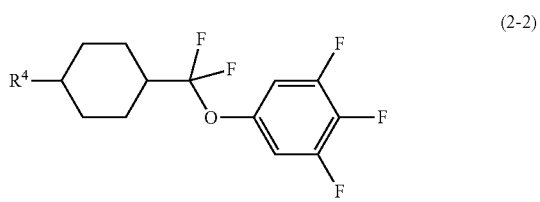

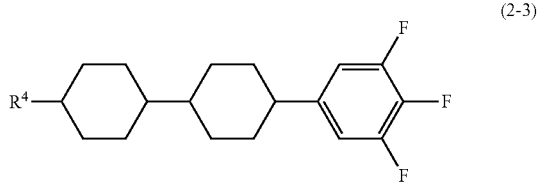

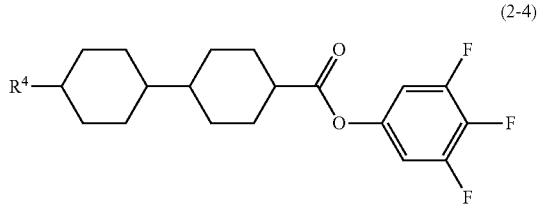

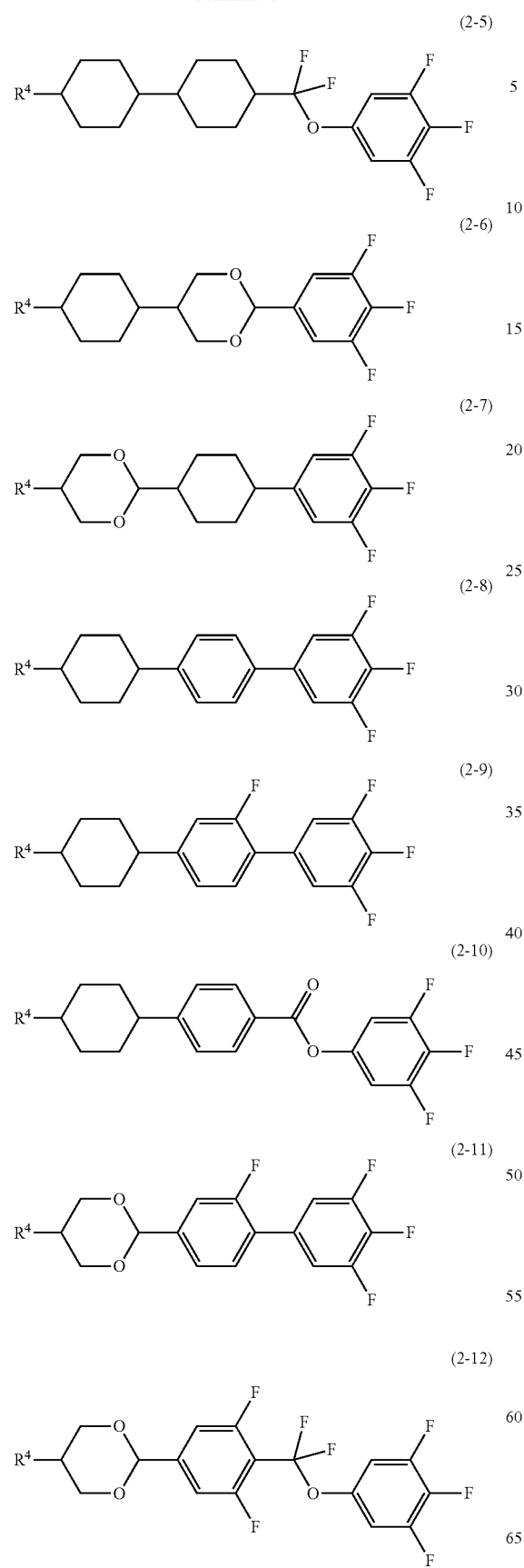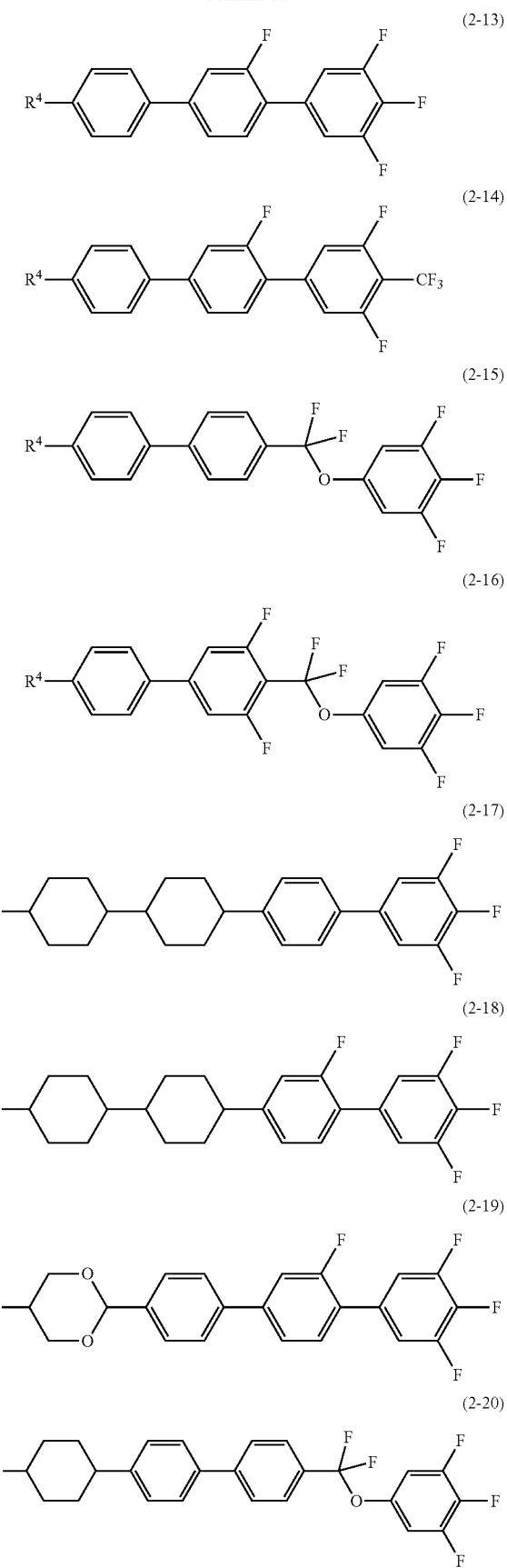

-continued (2-21)
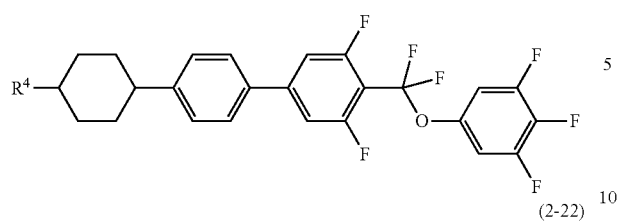

(2-22)
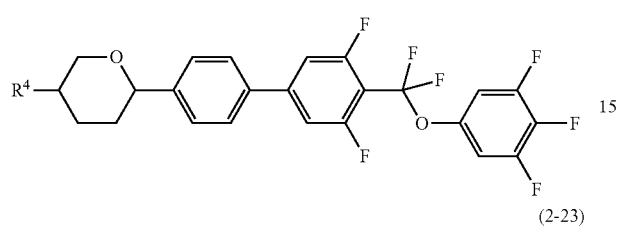

(2-23)
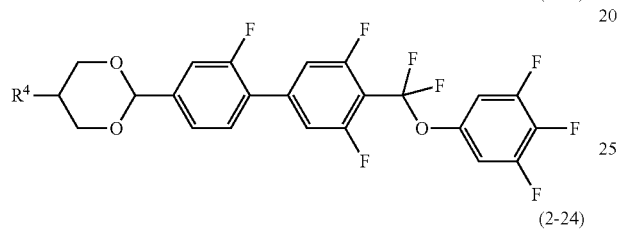

(2-24)
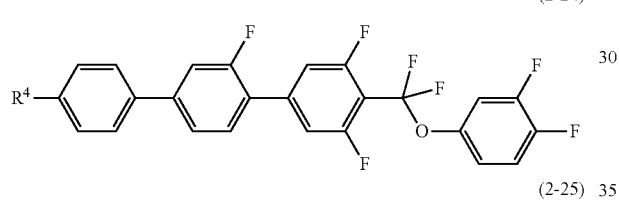

(2-25)
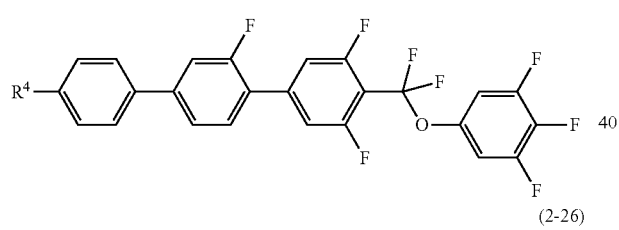

(2-26)
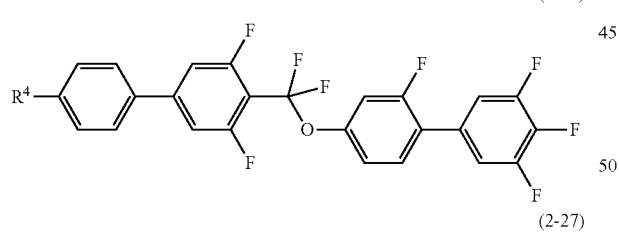

(2-27)
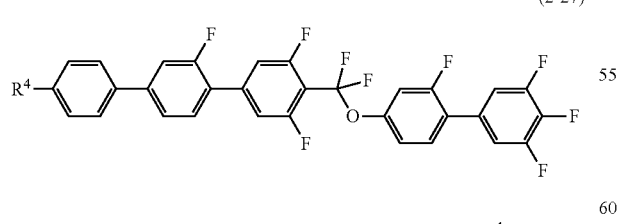

wherein, in formula (2-1) to formula (2-27), $R^4$ is alkyl having 1 to 12 carbons, alkoxy having 1 to 12 carbons or alkenyl having 2 to 12 carbons.

7. The liquid crystal composition according to claim 5, wherein a ratio of the second component is in the range of 10% by weight to 85% by weight based on the weight of the liquid crystal composition.

8. The liquid crystal composition according to claim 1, further containing at least one compound selected from the group of compounds represented by formula (3) as a third component:

(3)
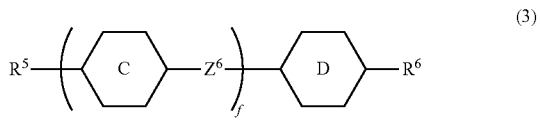

wherein, in formula (3), $R^5$ and $R^6$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring C and ring D are independently 1,4-cyclohexylene, 1,4-phenylene, 2-fluoro-1,4-phenylene or 2,5-difluoro-1,4-phenylene; $Z^6$ is a single bond, —CH$_2$CH$_2$—, —CH$_2$O—, —OCH$_2$—, —COO— or —OCO—; and f is 1, 2 or 3.

9. The liquid crystal composition according to claim 8, containing at least one compound selected from the group of compounds represented by formulas (3-1) to (3-13) as the third component:

(3-1)
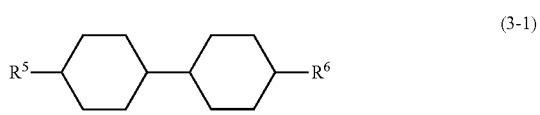

(3-2)
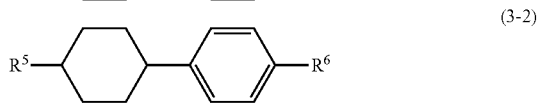

(3-3)
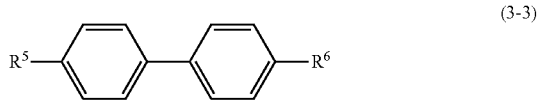

(3-4)
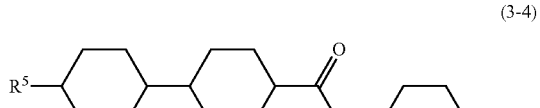

(3-5)
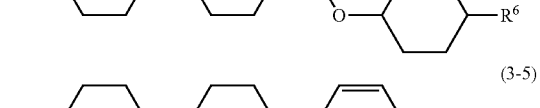

(3-6)
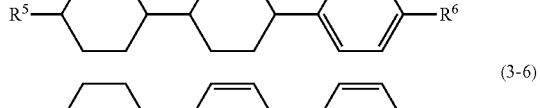

(3-7)
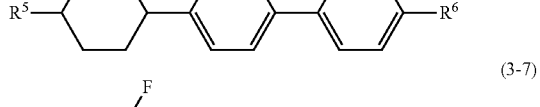

(3-8)
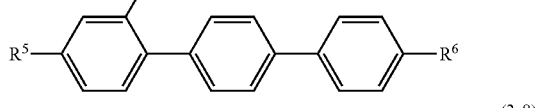

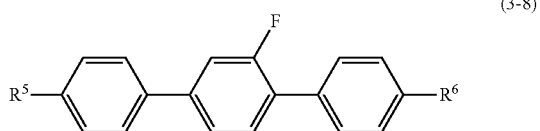

-continued

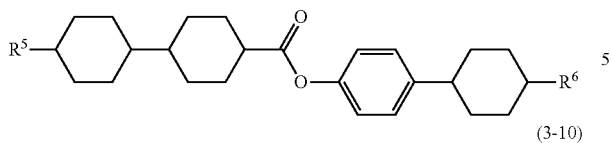
(3-9)

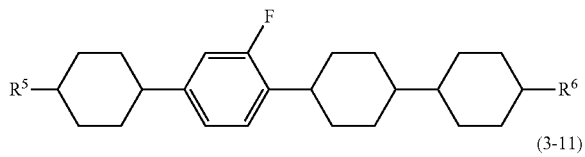
(3-10)

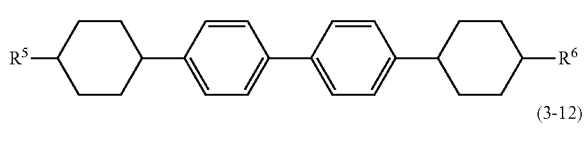
(3-11)

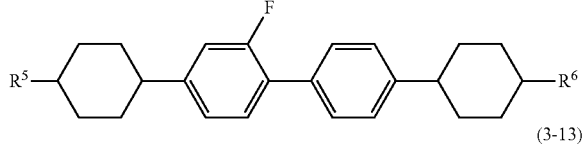
(3-12)

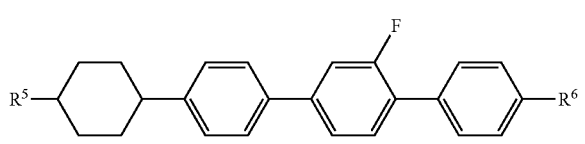
(3-13)

wherein, in formula (3-1) to formula (3-13), $R^5$ and $R^6$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

10. The liquid crystal composition according to claim 8, wherein a ratio of the third component is in the range of 5% by weight to 70% by weight based on the weight of the liquid crystal composition.

11. The liquid crystal composition according to claim 1, containing at least one polymerizable compound selected from the group of compounds represented by formula (4) as an additive component:

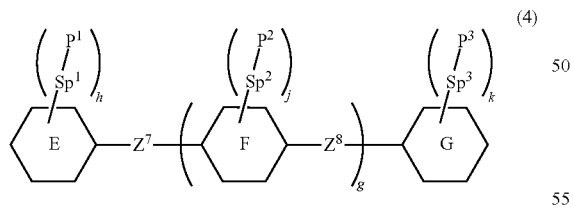
(4)

wherein, in formula (4), ring E and ring G are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; ring F is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; $Z^7$ and $Z^8$ are independently a single bond or alkylene having 1 to 10 carbons, and in the alkylene, at least one of —$CH_2$— may be replaced by —O—, —CO—, —COO— or —OCO—, and at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine; $P^1$, $P^2$ and $P^3$ are a polymerizable group; $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine; g is 0, 1 or 2; and h, j and k are independently 0, 1, 2, 3 or 4, and a sum of h, j and k is 1 or more.

12. The liquid crystal composition according to claim 11, wherein, in formula (4) described in claim 11, $P^1$, $P^2$ and $P^3$ are independently a polymerizable group selected from the group of groups represented by formulas (P-1) to (P-5):

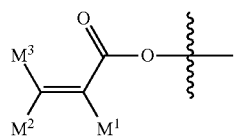
(P-1)

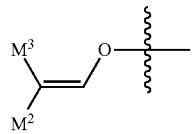
(P-2)

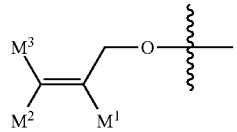
(P-3)

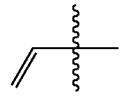
(P-4)

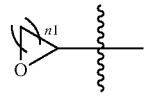
(P-5)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (P-5), $n^1$ is 1, 2, 3 or 4; when both $P^1$ and $P^3$ are a group represented by formula (P-4), at least one of Sp¹ and Sp³ is alkylene in which at least one of —CH₂— is replaced by —O—, —COO—, —OCO— or —OCOO—.
13. The liquid crystal composition according to claim 11, containing at least one polymerizable compound selected from the group of compounds represented by formulas (4-1) to (4-27) as the additive component:
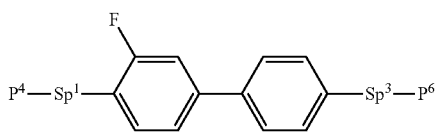
(4-1)
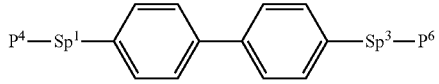
(4-2)
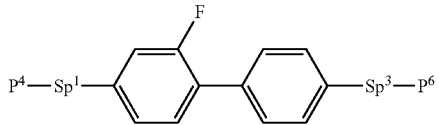
(4-3)
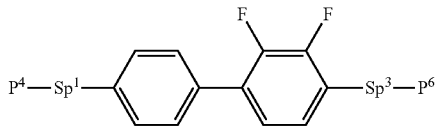
(4-4)
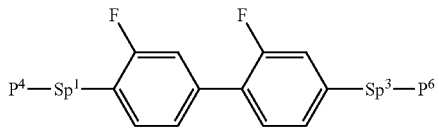
(4-5)
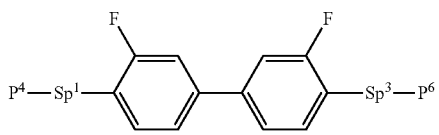
(4-6)
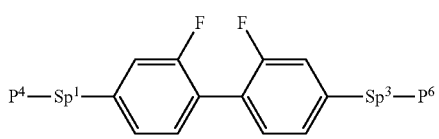
(4-7)
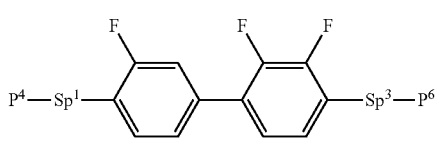
(4-8)
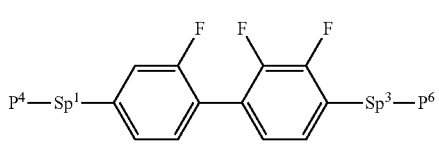
(4-9)
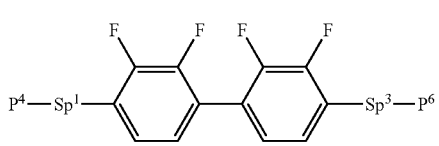
(4-10)
-continued
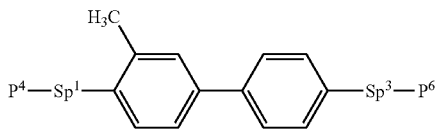
(4-11)
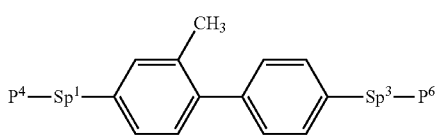
(4-12)
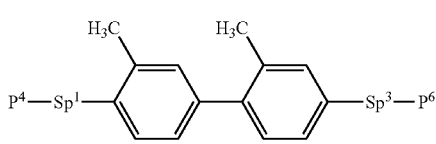
(4-13)
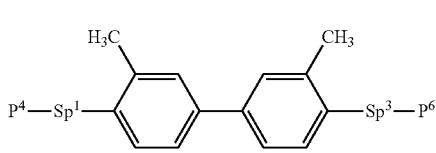
(4-14)
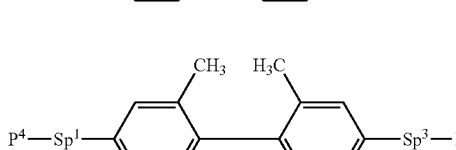
(4-15)
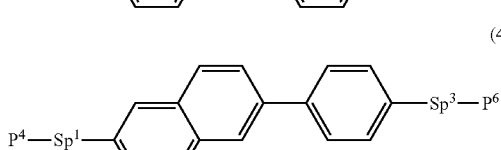
(4-16)
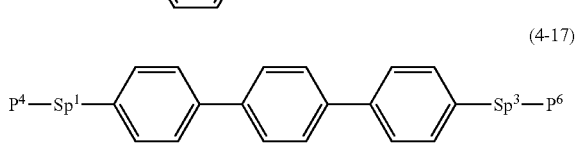
(4-17)
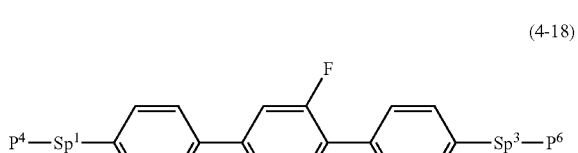
(4-18)
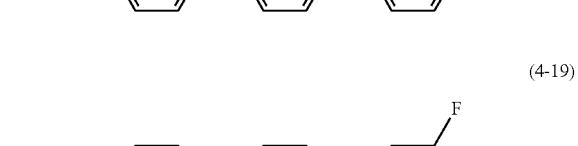
(4-19)
(4-20)

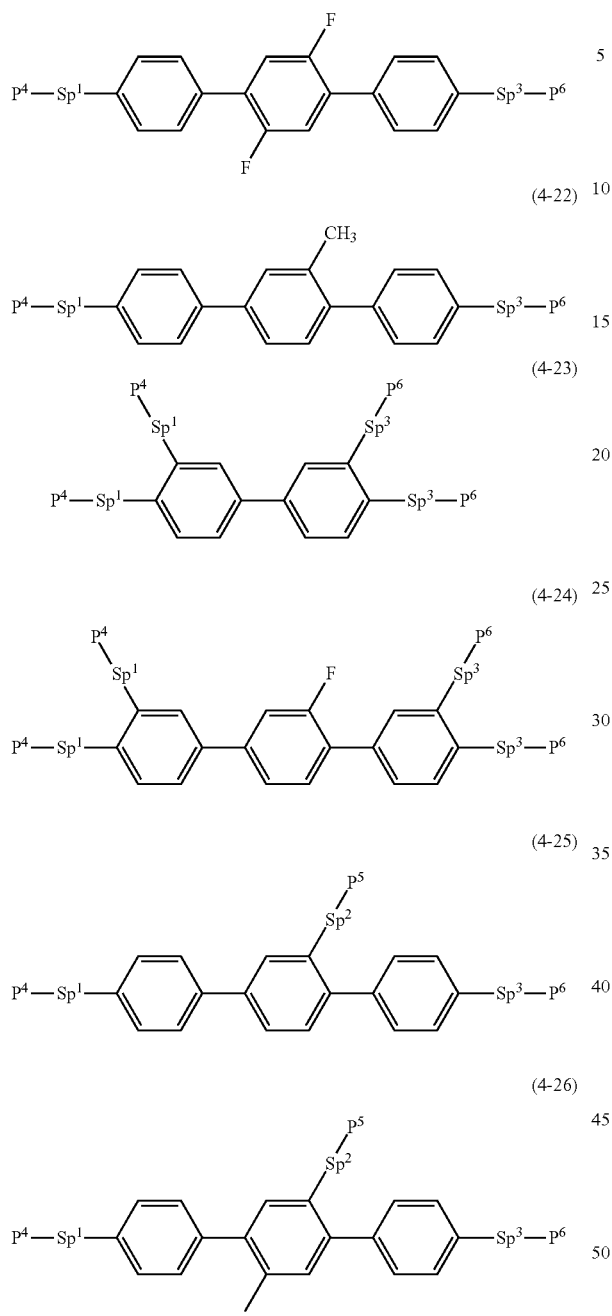
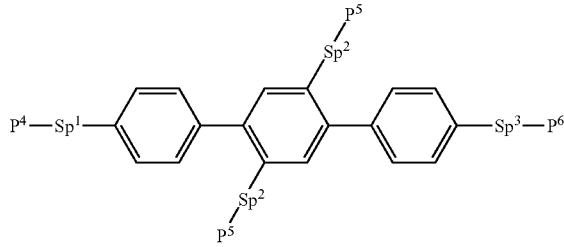

wherein, in formula (4-1) to formula (4-27), $P^4$, $P^5$ and $P^6$ are independently a group represented by formulas (P-1) to (P-3);

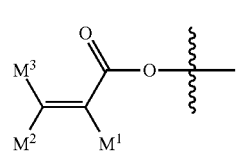

(P-1)

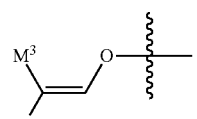

(P-2)

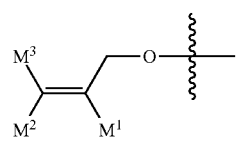

(P-3)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (4-1) to formula (4-27), $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine.

14. The liquid crystal composition according to claim 11, wherein a ratio of addition of the additive component is in the range of 0.03% by weight to 10% by weight, based on the weight of the liquid crystal composition before adding an additive thereto.

15. A compound represented by formula (1):

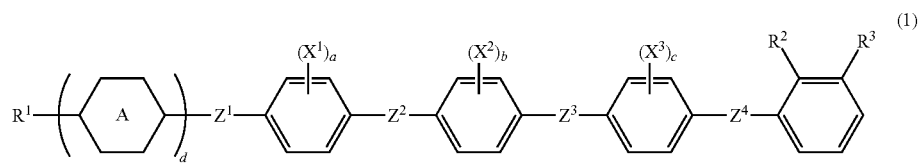

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, and one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen is replaced by fluorine; $Z^1$, $Z^2$, $Z^3$ and $Z^4$ are independently a single bond, —CH$_2$CH$_2$—, —CH$_2$O—, —OCH$_2$—, —COO—, or —OCO—; a, b and c are independently 0, 1, 2, 3 or 4, wherein a sum of a, b and c is one or more; and d is 0, 1 or 2.

16. The compound according to claim 15, represented by any one of formulas (1-1) to (1-3):

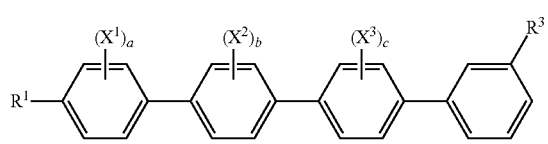

(1-1)

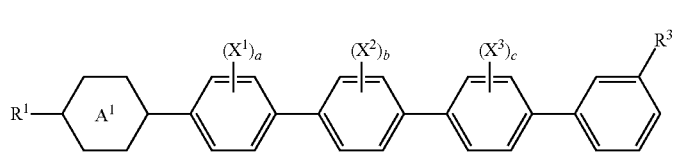

(1-2)

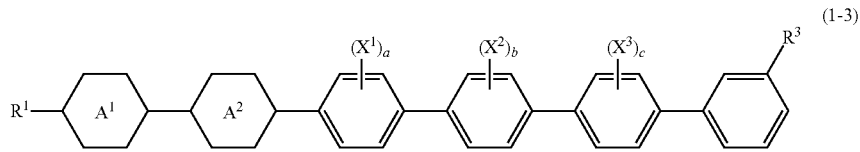

(1-3)

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine or chlorine; and a, b, and c are independently 0, 1, 2, 3 or 4, wherein a sum of a, b and c is one or more.

17. The compound according to claim 15, represented by any one of formulas (1-1-1) to (1-1-9), formula (1-2-1) and formula (1-2-2):

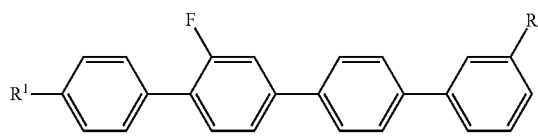

(1-1-1)

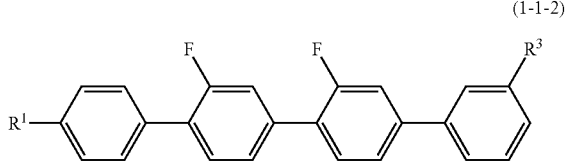

(1-1-2)

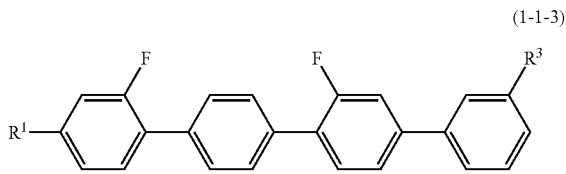

(1-1-3)

-continued

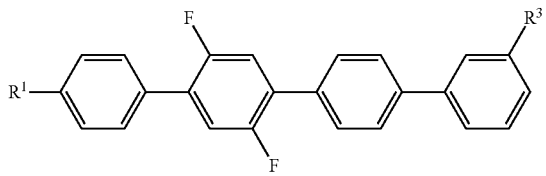

(1-1-4)

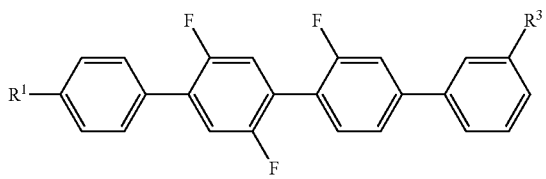

(1-1-5)

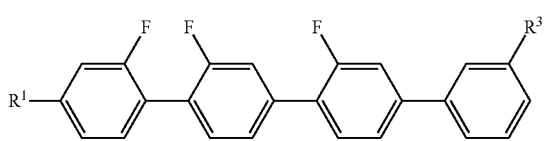

(1-1-6)

-continued

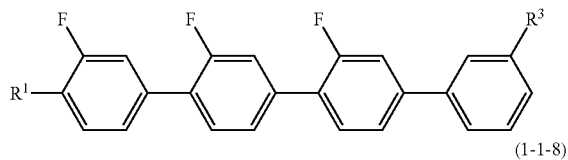
(1-1-7)

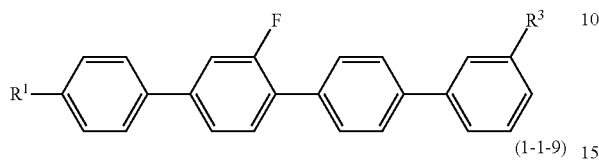
(1-1-8)

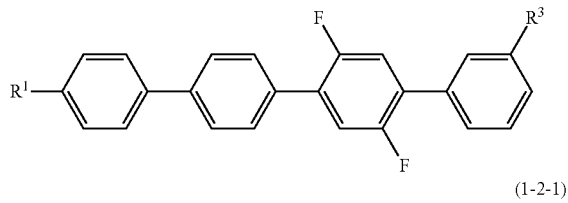
(1-1-9)

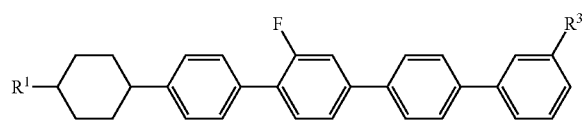
(1-2-1)

-continued

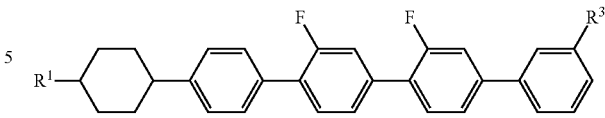
(1-2-2)

wherein, in formulas (1-1-1) to (1-1-9), formula (1-2-1) and formula (1-2-2), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

18. A liquid crystal display device, including the liquid crystal composition according to claim 1.

19. The liquid crystal display device according to claim 18, wherein an operating mode in the liquid crystal display device is an IPS mode, a VA mode, an FFS mode or an FPA mode, and a driving mode in the liquid crystal display device is an active matrix mode.

20. A polymer sustained alignment mode liquid crystal display device, wherein the liquid crystal display device includes the liquid crystal composition according to claim 11, and a polymerizable compound in the composition is polymerized.

* * * * *